United States Patent [19]
Shabot et al.

[11] Patent Number: 5,942,986
[45] Date of Patent: Aug. 24, 1999

[54] SYSTEM AND METHOD FOR AUTOMATIC CRITICAL EVENT NOTIFICATION

[75] Inventors: Myron M. Shabot, Culver City; Mark Lobue, Palm Dale, both of Calif.

[73] Assignee: Cedars-Sinai Medical Center, Los Angeles, Calif.

[21] Appl. No.: 08/512,887

[22] Filed: Aug. 9, 1995

[51] Int. Cl.$^6$ .............................. H04Q 7/18; G06F 17/00; G06F 159/00

[52] U.S. Cl. .................................. 340/825.44; 340/311.1; 340/539; 340/825.45; 370/313; 600/523; 600/513; 600/515; 379/38; 706/924

[58] Field of Search ........................ 340/825.44, 825.47, 340/311.1, 825.69, 870.01, 539, 825.45; 455/31.1, 426; 379/38; 364/224.5, 224.6, 224.7, 276, 922, 922.2, 922.3, 922.4; 128/903, 904; 283/900; 370/310, 313, 314; 600/523, 513, 300, 438, 515; 706/924

[56] References Cited

U.S. PATENT DOCUMENTS

| | | | |
|---|---|---|---|
| 4,751,726 | 6/1988 | Hepp et al. | 379/93 |
| 5,003,984 | 4/1991 | Muraki et al. | 600/523 |
| 5,036,852 | 8/1991 | Leishman | 128/630 |
| 5,128,979 | 7/1992 | Reich et al. | 379/40 |
| 5,228,449 | 7/1993 | Christ et al. | 128/691 |
| 5,307,263 | 4/1994 | Brown | 364/413.09 |
| 5,319,355 | 6/1994 | Russek | 128/903 X |
| 5,331,549 | 7/1994 | Crawford, Jr. . | |
| 5,348,008 | 9/1994 | Bornn et al. | 600/523 X |
| 5,357,427 | 10/1994 | Langen et al. | 364/413.02 |
| 5,390,238 | 2/1995 | Kirk et al. | 379/93 |
| 5,404,292 | 4/1995 | Hendrickson | 364/413.02 |
| 5,416,695 | 5/1995 | Stutman et al. | 364/413.02 |

(List continued on next page.)

OTHER PUBLICATIONS

Motorola,"PMR 2000 Personal Message Receiver" 340/825.44 No Mmth, 1986.

Shabot, M. Michael et al.; "Decision Support Systems in Critical Care"; Springer–Verlag; 1994. No Month.

"HP CareVue 9000;" Hewlett Packard brochure; 1989. NoMonth.

"HP Unveils New Era in Physician Access to Patient–Monitoring Data"; Hewlett Packard News, May 24, 1995.

(List continued on next page.)

Primary Examiner—Edwin C. Holloway, III
Assistant Examiner—William H. Wilson, Jr.
Attorney, Agent, or Firm—Pretty, Schroeder & Poplawski, P.C.

[57] ABSTRACT

A critical event notification system continuously monitors patient statistics and lab data to detect critical events, and automatically pages a responsible physician or physicians, each having an alphanumeric pager. In particular, a computer is used to continually access real-time data and multiple hospital databases which are periodically updated. These databases include patient chart databases, databases corresponding to patient history and databases maintained by various labs. The computer, preferably a clinical information system, is automatically provided with certain data, or periodically extracts it from other, relational databases. The computer automatically reviews this data, makes the critical event determination, and formulates an alphanumeric message that is informative as to the patient's condition and the reasons why a critical event was detected. After automatically retrieving from a database a personal identification number ("PIN") for a remote pager of each physician responsible for the patient, the computer automatically establishes modem contact with a paging network, and causes the network to page each responsible physician and transmit to them the alphanumeric message. The alphanumeric message preferably indicates patient name, diagnosis, the event prompting the page, and the name and return telephone number of medical personnel at the hospital who are attending the particular patient.

25 Claims, 11 Drawing Sheets

U.S. PATENT DOCUMENTS

| | | | |
|---|---|---|---|
| 5,430,440 | 7/1995 | Shim | 340/825.44 |
| 5,447,164 | 9/1995 | Shaya et al. | 128/710 |
| 5,544,661 | 8/1996 | Davis et al. | 128/904 X |
| 5,549,113 | 8/1996 | Halleck et al. | 128/903 X |
| 5,576,952 | 11/1996 | Stutman et al. | 364/413.02 |
| 5,579,001 | 11/1996 | Dempsey et al. | 340/870.01 |
| 5,579,775 | 12/1996 | Dempsey et al. | 128/903 X |
| 5,592,945 | 1/1997 | Fielder | 600/523 |
| 5,740,800 | 4/1998 | Hendrickson et al. | 600/300 |

OTHER PUBLICATIONS

Shabot, M. Michael et al.; "Inferencing Strategies for Automated Alerts on Critically Abnormal Laboratory and Blood Gas Data"; The Computer Society of the IEEE; 1989 pp. 54–57 No Month.

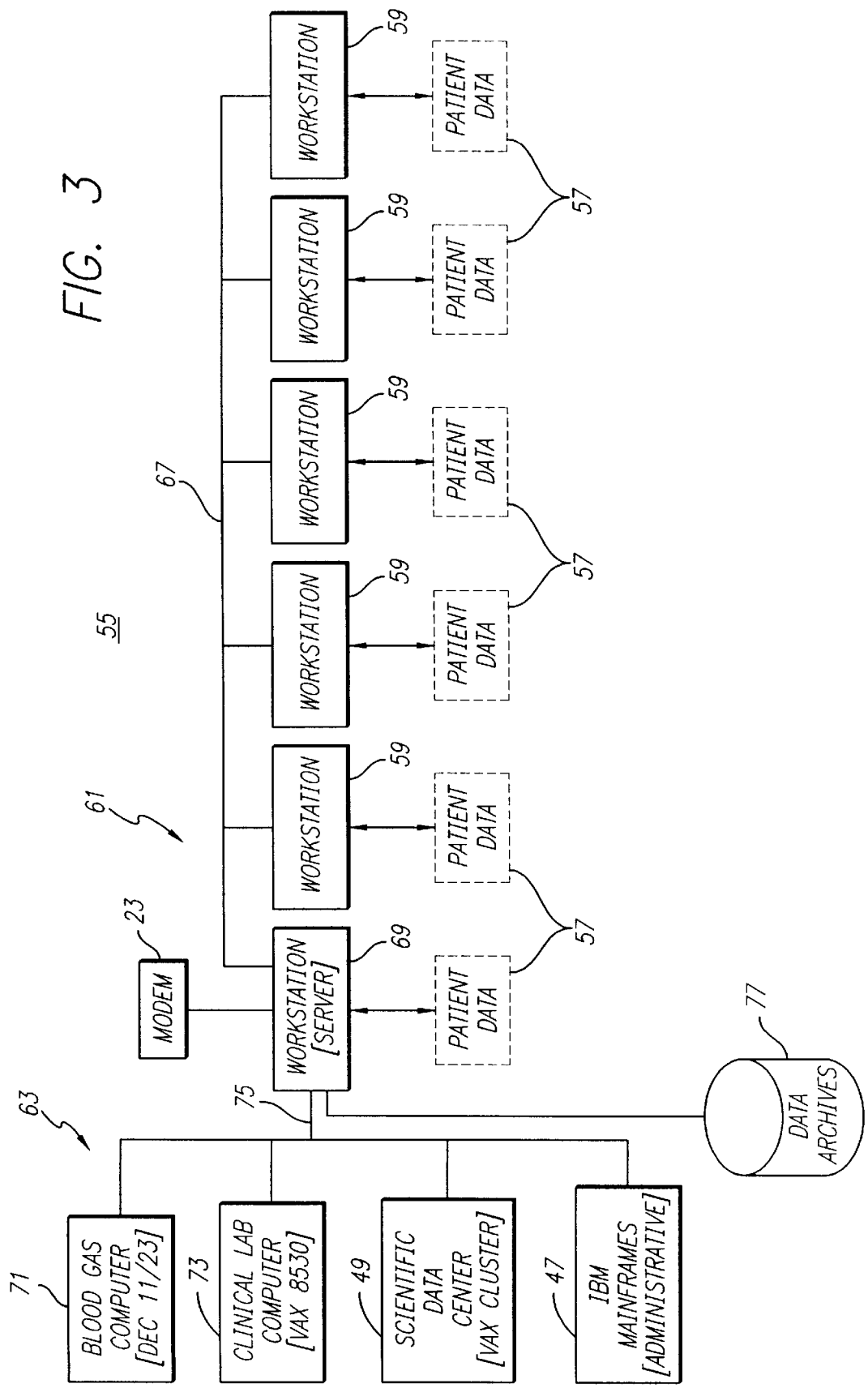

FIG. 6
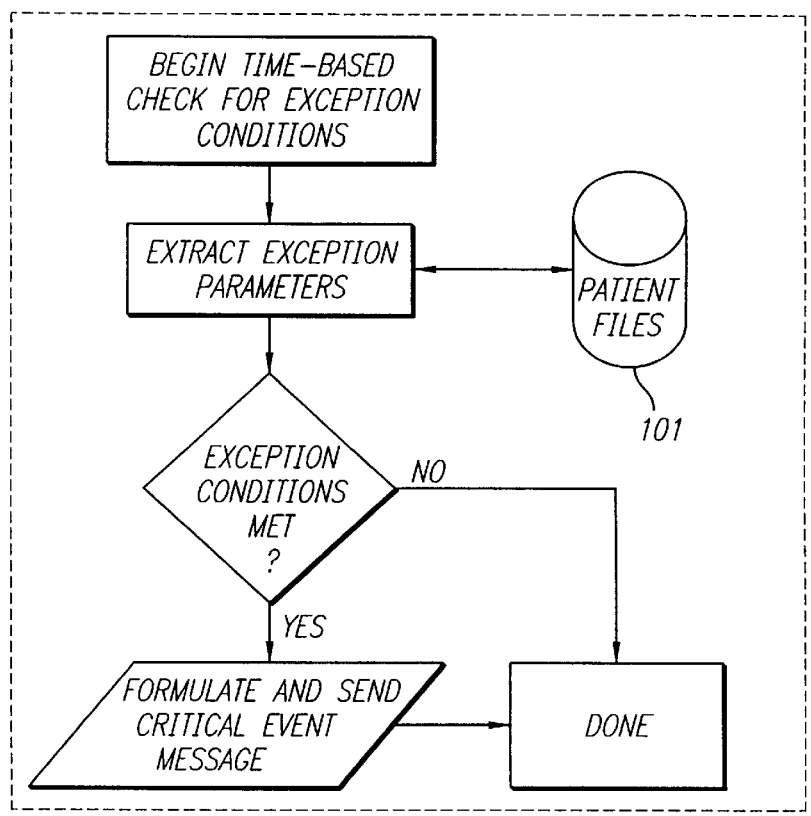
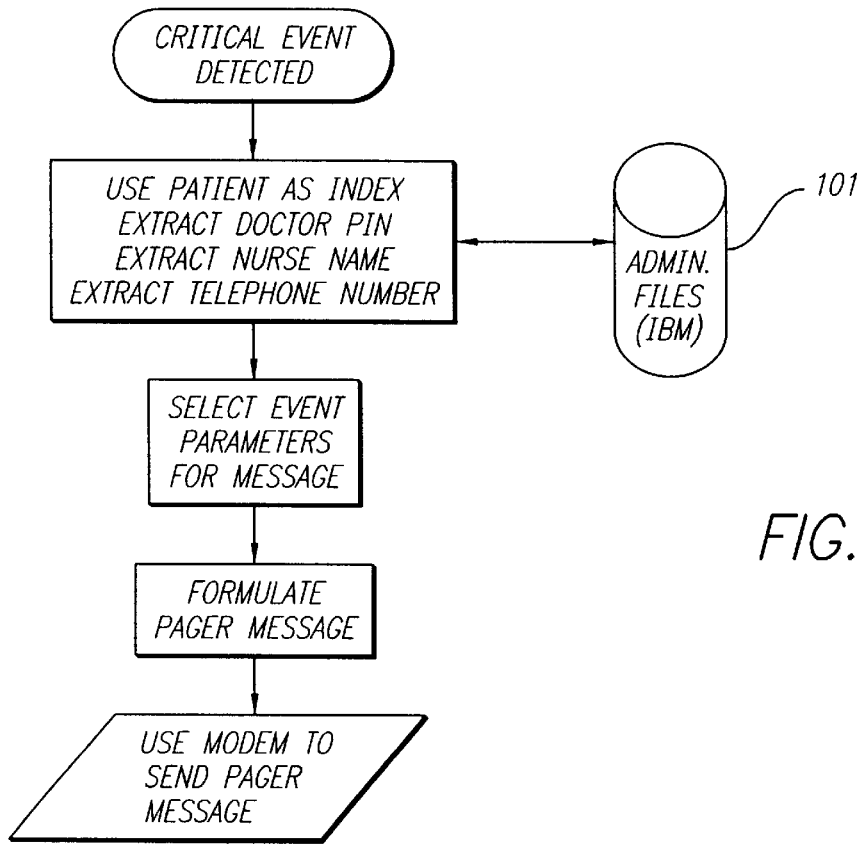
FIG. 7

FIG. 10

```
HP StarLink                View Message (732/746)      03/25/95  12:16 pm
03/24/95   7:11 am                                              000.000

43- EXCEPTION REPORT PATIENT, JOHN Q.  040999111
Dx: Vascular /neurologic /hemodynamic monitoring S/P Rt.
Carotid
7ICU 2 Age: 84  Day:  1   Codes:  VA  APACHE:  30

Conditions: FiO2 > 60% for 4 Hrs;peep >= 15

[Help]  [Mute]    [Discard]    [Prev]  [Next]    [Done]
```

FIG. 11

```
HP StarLink                View Message (637/873)      04/01/95  2:36 am
                           No Receiver Card
03/14/95   6:14 am              [New]                           000.000

50-** ALERT VALUE ** (pH  <  7.25)
JOHN Q. 040999111 7ICU 2
pHa 6.99 @06:/00  03/14/95

[Help]  [Mute]    [Discard]    [Prev]  [Next]    [Done]
```

FIG. 12-1

Bed: 1 8246  Admit Date: 06/12/95  Service: GS  Attending Physician:

|   |   |                    | 12Jun95 0700 | 0800 | 0900 | 1000 | 1100 | 1200 | 1300 |
|---|---|--------------------|--------------|------|------|------|------|------|------|
| L | C | Hemoglobin         |              |      |      |      | 5 11.5 |    |      |
| a | B | Hematocrit         |              |      |      |      | 33.1 |      |      |
| b | C | Platelet Count     |              |      |      |      | 6 145000 |  |      |
| s |   | WBC                |              |      | 1    |      | 7 11.7 |    |      |
|   |   | Polys              |              |      | 70   |      |      |      |      |
|   |   | Bands              |              |      |      |      |      |      |      |
|   |   | Lymphocytes        |              |      | 1 24 |      |      |      |      |
|   |   | Monocytes          |              |      | 1 6  |      |      |      |      |
|   |   | Eosinophils        |              |      |      |      |      |      |      |
|   |   | Basophils          |              |      |      |      |      |      |      |
|   |   | Atypical Lymphs    |              |      |      |      |      |      |      |
|   |   | Myelocytes         |              |      |      |      |      |      |      |
|   |   | Metamyelocytes     |              |      |      |      |      |      |      |
|   | C | PT                 |              |      |      |      | 15.3 |      |      |
|   | O | Int'l Norm'd Ratio |              |      |      |      | 1.6  |      |      |
|   | A | % Activity PT      |              |      |      |      |      |      |      |
|   | G | PTT                |              |      |      |      | 8 24 |      |      |
|   | S | Fibrinogen         |              |      |      |      |      |      |      |
|   |   | Fibrin Monomers    |              |      |      |      |      |      |      |
|   |   | Fibrin Split       |              |      |      |      |      |      |      |
|   |   | Thrombin Time      |              |      |      |      |      |      |      |
|   |   | Bleeding Time      |              |      |      |      |      |      |      |
|   | C | Na+                |              |      |      |      | 145  |      |      |
|   | H | K+                 |              |      |      |      | 3.7  |      |      |
|   | E | Cl-                |              |      |      |      | 103  |      |      |
|   | M | HCO3-              |              |      |      |      | 9 23 |      |      |
|   | I | BUN                |              |      |      |      | 54   |      |      |
|   | S | Creatinine         |              |      |      |      | 10 3.2 |    |      |
|   | T | Glucose            |              |      |      |      | 794  |      |      |
|   | R | Ca++               |              |      | 2 10.5 |    | 11 5.5 |    |      |
|   | Y | Phosphate          |              |      |      | 3.7  |      |      |      |

| | | | | | | | |
|---|---|---|---|---|---|---|---|
| Uric Acid | | | | | | | |
| Bilirubin Total | | | | 5.2 | | | |
| Bilirubin Direct | | | | 0.5 | | | |
| Bilirubin Indirect | | | | [12]TOTAL B | | | |
| Total Protein | | | | [13]NOT CAL | | | |
| Albumin | | | | 4.5 | | | |
| Globulin | | | | 2.7 | | | |
| LDH | | | | | | | |
| Alk Phos | | | | 44 | | | |
| SGOT | | | | 55 | | | |
| SGPT | | | | 23 | | | |
| Lactate | | | | 11.6 | | | |
| A  FiO2 | | | [2] 1.00 | | [14] 1.00 | [15] 0.60 | |
| B  O2 L/m | | | | | | | |
| G  pHa | | | [3] 7.03 | | [14] 7.40 | [15] 7.44 | |
| -  PaO2 | | | [4] 293 | | [14] 407 | [15] 156 | |
| s  PaCO2 | | | [3] 31 | | [14] 38 | [15] 33 | |
|    HCO3 | | | [9] 8.0 | | [14] 24.0 | [15] 22.0 | |
|    SaO2 | | | [3] 100 | | [14] 100 | [15] 100 | |
| FiO2-v | | | | | | | |

Labs continued on the next page...

Printed: Jun 12 95 1345    RN Signature(s): _____    Time _____

Labs continued from previous page...

| | 12Jun95 0700 | 0800 | 0900 | 1000 | 1100 | 1200 | 1300 | | | | |
|---|---|---|---|---|---|---|---|---|---|---|---|
| L V pHv | | | | | | | | | | | |
| a B PvO2 | | | | | | | | | | | |
| b G PvCO2 | | | | | | | | | | | |
| s . HCO3 - Venous | | | | | | | | | | | |
| s SvO2 | | | | | | | | | | | |
| E CPK | | | | | 329 | | | | | | |
| N CKMB | | | | | | | | | | | |
| Z Relative Index | | | | | | | | | | | |
| Y LDN Isoenzymes | | | | | | | | | | | |
| M Amylase | | | | | 851 | | | | | | |
| E Lipase | | | | | 1.6 | | | | | | |
| S Mg++ | | | | | | | | | | | |
| Ammonia | | | | | | | | | | | |
| GGT | | | | | | | | | | | |
| Osmolarity | | | | | | | | | | | |
| D Dilantin | | | | | | | | | | | |
| R Theophylline | | | | | | | | | | | |
| U Phenobarbital | | | | | | | | | | | |
| G Quinidine | | | | | | | | | | | |
| L Lidocaine | | | | | | | | | | | |
| E Procainamide | | | | | | | | | | | |
| V NAPA | | | | | | | | | | | |
| E Pro NAPA | | | | | | | | | | | |
| L Digoxin | | | | | | | | | | | |
| S Thiocyanate | | | | | | | | | | | |
| Gentamicin | | | | | | | | | | | |
| Tobramycin | | | | | | | | | | | |
| Cyclosporin (WB) | | | | | | | | | | | |
| Cyclosporin (PL) | | | | | | | | | | | |
| Vancomycin | | | | | | | | | | | |

| | | | | | | | | | |
|---|---|---|---|---|---|---|---|---|---|
| W | Calcium, Free | | | | | | | | |
| B | Glucose (WB) | | | | | | | | |
| L | K+ (WB) | | | | | | | | |
| D | Na+ (WB) | | | | | | | | |
| U | Specific Gravity | | | | | | | | |
| A | Urine pH | | | | | | | | |
| | Protein (Urine) | | | | | | | | |
| | Glucose (Urine) | | | | | | | | |
| | Ketone (Urine) | | | | | | | | |
| | Hemoglobin (Urine) | | | | | | | | |
| T | Blood Tox Screen | | | | | | | | |
| O | Gastric Tox Screen | | | | | | | | |
| X | Misc Tox Screen | | | | | | | | |
| S | ETOH Tox Screen | | | | | | | | |
| C | Urine Tox Screen | | | | | | | | |
| | Documented by | | | | | 0.77 | | | |
| | | CLAB | | | | CLAB | | CLAB | CLAB |

1. 0920           (CLAB - 1121)
2. 0940           (CLAB - 1228)
3. 0940           (CLAB - 1121)
4. 0940
   ALERT VALUE (HCO3 < 18)   (CLAB - 1121)
5. RESULT REPEATED AND VERIFIED (CLAB -1137)
6. RESULT REPEATED AND VERIFIED (CLAB -1137)
7. RESULT REPEATED AND VERIFIED (CLAB -1137)
8. HEPARIN THERAPEUTIC RANGE: 58-85 S EC (CLAB - 1142)
9. RESULT REPEATED AND VERIFIED NOTE: NEW REFERENCE RANGE (CLAB - 1148)
10. NOTE: NEW REFERENCE (CLAB - 1145)
11. CRITICAL VALUE    (CLAB - 1207)
12. TOTAL BILIRUBINS LESS THAN 1.0 MG/DL ARE NOT FRACTIONATED. (CLAB - 1200)
13. NOT CALCULATED   (CLAB - 1200)
14. 1105             (CLAB - 1121)
15. 1210             (CLAB - 1223)

ALERT VALUE (pH < 7.25)

FIG. 13-2

SYSTEM AND METHOD FOR AUTOMATIC CRITICAL EVENT NOTIFICATION

The present invention relates to a system and method for automatic critical event notification. In particular, its preferred embodiment provides a device that automatically interrogates hospital databases to examine patient data, and automatically pages physicians if it has determined that a critical event has occurred.

BACKGROUND

Computers and other electronic devices have revolutionized the practice of medicine in many hospitals.

For example, some hospitals feature computer workstations installed at many patient bedsides and nursing stations. These workstations sometimes utilize automated sensors, which are coupled to the workstations to provide continuous streams of electronic data regarding a patient's condition. This enables a nurse or hospital technician to display various types of data side-by-side for review, and also to periodically store the data as an electronic "chart," or as part of a permanent electronic record. For example, these systems may be connected to automatic sensors that measure levels of certain elements of a patient's blood, such as oxygen saturation. Other sensors that have been connected to these automatic computer monitoring systems include urimeters, respiratory sensors, heartbeat sensors, as well as other sensors.

Computer workstations of the type just described sometimes operate by receiving continuous data, which a nurse or technician may selectively sample and store in the patient's chart. For example, one typical mode of employing this equipment would be for the nurse to sample the continuous data representing the patient approximately every hour and cause the data to be entered permanently on the patient's electronic chart. When a physician responsible for the patient's care then reviews a hard-copy print-out of this chart, or reviews it on the workstation's display screen, the physician may issue appropriate orders relating to the patient's care.

Of course, electronic "beepers" and paging systems have also played an important role in medical care. They permit a nurse or other medical assistant to request that the physician immediately check-in with the nurse in response to an immediate patient condition. Recently, these "beepers" and paging systems have provided alphanumeric display capability using a liquid crystal display screen of the physician's beeper. Accordingly, a nurse can use a paging network to send the physician a message requesting a response from the physician. These paging systems are relatively easy to operate and may be sometimes operated directly from a nurse's workstation, e.g., by manually formatting an alphanumeric message and sending that message as an electronic mail message to a paging network. For example, a commercially-available system called "Starlink" permits a nurse or other person to type in a message using a computer keyboard, and send that message to a remote pager using a modem. The "Starlink" system provides a paging facility which receives this modem communication along with identifying information for the particular physician, which is looked up by the nurse and included as part of the modem transmission, and causes the alphameric message sent by the nurse to be transmitted to the particular physician's pager.

Computers and other electronic equipment such as those specific systems mentioned above have gone far to improve the quality and nature of medical care, but they still rely on significant human interaction if they are to function correctly. For example, there are occasions when a critical or sensitive condition of the patient will go unnoticed by a nurse or hospital technician, and not be reported to the physician. Other times, specific orders relating to a patient's symptoms may be issued for a patient, but due to a change in staff workshift, the condition might not always be properly recognized or properly reported to the physician. Lastly, sometimes the physician is diverted from attending to another patient, because hospital staff page the physician regarding mundane matters.

There is therefore an urgent need in the art for a system that automatically notifies a physician in response to predetermined events. Preferably, systems of this type would not be needed on an individual basis for each particular patient; rather, a need exists for a system capable of monitoring many patients, ascertaining the presence of critical or sensitive events should they occur, and automatically determining the identity of the physician or physicians to be notified of the condition. Finally, a need exists for a system that reviews many physical parameters to determine the existence of complex conditions, e.g., a bradycardia which persists beyond a defined length of time. The present invention solves these needs and provides many further related advantages.

SUMMARY

The present invention provides a critical event notification system that significantly enhances medical care. It permits review of a patient's diagnostic information, lab results, chart, or other data, automatically, by computer or similar equipment, and it provides for automatic paging of a responsible physician or physicians should a "critical event" be detected. That is to say, a decision to page an individual (a physician in the case of the preferred embodiment) is made automatically by the system, and does not require a direct human decision. As can be seen therefore, the present invention permits reduction in the number of pages by controlling paging directly in response to automatically detected critical events. In the context of medicine, it helps ensure that situations requiring the physician's attention will always be correctly and immediately recognized and reported to the physician via a technical and informative message. The present invention is not limited to medical care and physicians, and should present a wide range of applications outside of the medical profession.

One form of the invention provides a system that automatically notifies an individual of the existence of a critical value of a measurement parameter. It does this using a computer system that automatically monitors input data, a remote pager carried by the individual and a paging network that can page the individual using the remote pager. The computer system has a communications device that permits it to selectively communicate with the paging network and automatically page the remote pager. The computer system monitors the input data, either as it arrives or by performing periodic reviews of that data after it has been stored to a memory or logging device. The computer system automatically compares the data representing the measurement parameter with a predefined quantity. If it detects a predetermined relation, e.g., that the predefined quantity is greater than data representing the parameter, it thereby determines that a critical event has occurred. The computer system then electronically and automatically determines that the individual should be notified of the critical event, and causes the paging network to page the individual.

In the preferred embodiment of a medical device that automatically notifies physicians, discussed below, one critical event could be defined as a drop in a patient's calcium level (as determined from periodic analysis of the patient's blood) below a predetermined critical level, e.g., below ten milligrams per deciliter. In this example, the measurement parameter would be calcium level, and there could be many such parameters carried by the data, for example, phosphorus, oxygen, urea, nitrogen and/or magnesium levels. Each of these can be analyzed with respect to a critical event, e.g., when concentration of one of these elements falls above or below a predetermined level or between a range of values.

Instantaneous detection of whether a single parameter of input data meets a predefined relation (e.g., greater than, less than, equal to, between a range, etc.) is not the only application of the invention. Rather, the invention can also be used to automatically perform sophisticated review and analysis. As one example, the invention applies to monitor of several parameters simultaneously, and ascertain a critical event only when two conditions have been concurrently met (e.g., one parameter greater than a first value and a second parameter less than a second value). As another example, the invention can be applied to periodic review of stored data, e.g., determination of a critical event when a patient has been maintained on mechanical ventilation with a sixty percent or greater oxygen level for over four hours, with updates as to oxygen content being electronically provided by the ventilator periodically. In fact, the preferred embodiment (a medical paging system) is programmable to allow user definition of certain "exception" conditions which define a critical event, and these may be programmed on a patient by patient basis.

From the foregoing, it should be readily apparent that the present invention provides an important advance in the field of medicine. As but one example, a physician could have specialized monitoring of a patient with a heart condition, and be notified when conditions exist which might be normal for other patients or healthy individuals. The paging of the physician is automatic, and in further specific features of the invention, the paging includes an alphanumeric message that is displayed on a pager display screen. Formulation of this message is automatic, and the individual to be paged is immediately and informatively notified of the precise nature of the critical event. Using the example mentioned above, the physician could be notified that a patient's calcium level has dropped below eight milligrams per deciliter, and further, the precise calcium level, the patient's name and diagnosis, and the name of a nurse attending to the patient and his or her telephone number at the hospital.

In another more detailed feature of the invention, multiple pagers are used, each having a unique PIN number, and the individual to be notified of the critical event may vary depending upon the event. In the preferred embodiment, multiple patients may be monitored, and particular physicians paged depending upon the type of critical event and the identity of the patient. PIN numbers for each physician may be stored in a database or table in software, such that the computer system can analyze patient statistics and page the appropriate physicians. For example, if a particular patient suffers from an abnormally fast heartbeat ("tachyarrhythmia"), then a resident physician, an attending physician and a cardiologist on-call could each be paged. The resident and attending physicians would, in that example, be paged based upon their assignment to the particular patient, and the cardiologist would be paged based upon the particular condition.

The invention may be better understood by referring to the following detailed description, which should be read in conjunction with the accompanying drawings. The detailed description of a particular preferred embodiment, set out below to enable one to build and use one particular implementation of the invention, is not intended to limit the enumerated claims, but to serve as a particular example thereof.

BRIEF DESCRIPTION OF THE DRAWINGS

FIG. 3 illustrates the interconnection of several, linked computer systems and components; in particular, the clinical information system is composed of independent, linked workstations, which communicate with other computer systems and data archives through a server workstation. Each workstation monitors several patients, and automatically stores and analyzes patient data to detect critical events. External computer systems and the data archives (seen at the left side of FIG. 3), provide relational database data to the clinical information system, and vice-versa.

FIG. 6 illustrates in greater detail the operations associated with the parallelogram labelled "Analyze Data To Detect Exception Cond." of FIG. 2.

FIG. 7 illustrates in greater detail the operations associated with the parallelogram labelled "Formulate Pager Message" of FIG. 2.

FIG. 8 illustrates a routine that places pager messages formulated by the clinical information system into a queue for transmission into the pager network.

FIG. 9 illustrates a routine that retrieves pager messages from the queue of FIG. 8 and actually transmits those messages to the pager network.

FIG. 10 shows an alphanumeric display screen of a remote pager used by the preferred embodiment, and illustrates the format of one message sent in response to two simultaneous exception conditions (i.e., $FiO_2 > 60\%$ for four hours, PEEP>15).

FIG. 11 shows an alphanumeric display screen of a remote pager used by the preferred embodiment, and illustrates the format of one message sent in response to a critical flag, namely, where blood pH has fallen below the critical numerical value of 7.25, and is in fact 6.99.

FIG. 12 shows a first page of a flowsheet that indicates some of the medical parameters that are stored by the clinical information system of the preferred embodiment, parameters which can be automatically analyzed to detect critical events.

FIG. 13 shows a second page of the flowsheet of FIG. 12.

DETAILED DESCRIPTION

The invention summarized above and defined by the enumerated claims may be better understood by referring to the following detailed description, which should be read in conjunction with the accompanying drawings. This detailed description of a particular preferred embodiment, set out below to enable one to build and use one particular implementation of the invention, is not intended to limit the enumerated claims, but to serve as a particular example thereof. The particular example set out below is the preferred specific implementation of a critical event notification system, namely, one that uses conventional pieces of equipment such as a pager network, remote alphanumeric pagers, computer systems and modems. The invention, however, may also be applied to other types of systems and equipment as well.

I. Introduction To The Principal Parts

Figure 1:
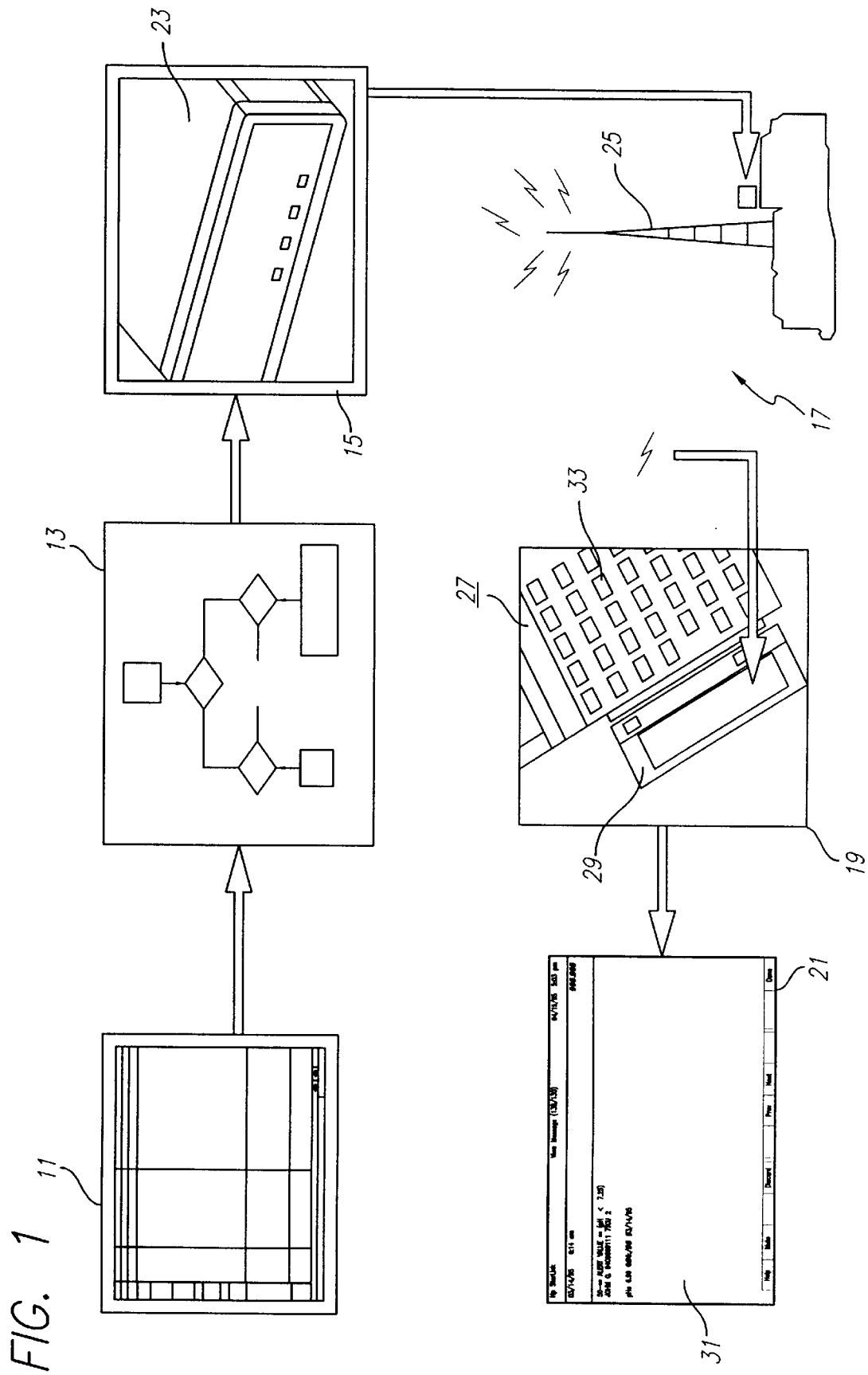
FIG. 1 is an illustrative diagram of the preferred embodiment, showing use of a clinical information system, automatic alert algorithms which monitor patient data to detect critical events, and a pager network.

FIG. 1 is an illustrative diagram of the preferred embodiment, showing use of a clinical information system, automatic alert algorithms, which monitor patient data to detect critical events, and a pager network. In particular, six pictorial blocks 11, 13, 15, 17, 19 and 21 are shown in FIG. 1 to help illustrate the operation of the preferred embodiment. They also help show how the present system automatically monitors patient data, detects the occurrence of critical events, and automatically notifies a physician. To perform this notification, the system automatically formats pager messages, as necessary, and itself automatically makes the decision to page the physician. The six blocks of FIG. 1 will be discussed in clockwise order, beginning at the top left, and proceeding in the direction of the various arrows seen in that figure.

The clinical information system monitors the patients and runs the alerting algorithms that make the decision to page. It consists of a commercially available computer network, namely, a CareVue 9000 System, available from the Hewlett-Packard Company. This system has a number of autonomous, but networked, computer workstations that execute software and supervise patient data for a large number of patients. The system may be used only for extremely ill patients who require continuous monitoring, for example, patients in ICU or CCU ("Cardiologic Care Unit"), or it could also be applied hospital-wide. One or more workstations also serves as a "server" workstation, and can interface through a second network with a number of other computer systems and databases. Each workstation display receives both continuous data inputs for certain patient statistics, e.g., pulse, and also periodic data, for example, representing lab results, such as enzyme production, drug levels, blood cell counts, etc., when they are available. Each workstation is also visually supervised by a nurse, who reviews the continuous data inputs and selectively samples them, e.g., "charts" them, when the continuous data is representative of the patient's condition. Thus, for example, certain patient statistics are periodically sampled and stored by the workstation (under the nurse's control) in a patient file at selected time intervals, for example, each ten minutes, each hour, etc.

A typical display screen for one of the workstations is seen in the first block 11 of FIG. 1. In that display screen, one patient's file or chart is seen, with the columns of the display representing regular time intervals (e.g., each hour, half-hour, etc.) and the rows representing patient statistics which have been sampled, or provided by an external computer system maintained by one of the hospital's labs. The rows typically include vital signs, such as respiration rate, temperature, heart rate, cardiac output and other statistics; they also typically include patient urine statistics, IV fluid intake, respirator oxygen percentage and volume, hemoglobin, blood calcium and potassium levels, etc.

The second block 13 of FIG. 1 represents alerting algorithms that are used by the server workstation of the clinical information system, some at periodic intervals, some each time new data is received. In particular, the server workstation provides an interface between the clinical information system and the other computer systems. Each time new data for a patient is reported to the clinical information system by an external computer (e.g., a blood gas computer or a clinical lab computer), that data is then distributed by the server workstation to the particular workstation corresponding to the patient. The data is then incorporated into the patient's chart. The server workstation also interfaces the clinical information system with an archives database (e.g., a computer mass storage device), so that patient data can be periodically stored in and retrieved from patient files maintained in the archives database.

The alerting algorithms, as mentioned, are of two types. First, some algorithms are used to detect critical events represented by incoming lab data, as that data is distributed by the server workstation to the particular workstation corresponding to the patient. While the server workstation distributes this data, the alerting algorithms review the data to determine if a "critical event flag" has been placed in the data by the hospital lab. Second, the server workstation also employs algorithms that periodically import selected data from patient files or particular workstations, as a logical unit of work, in order to perform more complex analysis, e.g., the detection of "exception conditions." For example, one exception condition is the state of a ventilator patient requiring a sixty percent or greater oxygen level for more than four hours. This type of analysis cannot be performed upon instantaneous measurements, such as upon only one data measurement obtained from hospital lab and distributed by the server workstation, and so, the analysis is performed on a periodic basis.

The clinical information system and other hospital systems are structured as relational databases, which permit the server workstation and other hospital computer systems to import and export data from databases all over the hospital as part of a logical unit of work. Thus, the clinical information system has access to all of the computer data that it needs to complete its sophisticated review, and is not limited to a review of data that is stored by any one particular workstation or group of them. To obtain this data, the server workstation formats a request for a particular type of data, which it addresses to a computer system or database possessing that data.

When the server workstation detects a critical event for a particular patient, either via a critical event flag (e.g., abnormal measurement data) or via the existence an exception condition (periodic patient file analysis), it automatically and immediately pages the responsible physician or physicians. To do this, the server workstation formulates an alphanumeric message that (1) identifies the patient and preliminary diagnosis (the medical ailment of the patient), (2) the particular critical event that has occurred and other critical alphanumeric information related to that critical event, and (3) provides the physician with the name of the responsible nurse at the hospital and a telephone number by which the physician can contact the nurse. The server workstation then dials a pager network via modem 23, as seen in the third block 15 of FIG. 1. The information automatically formulated and sent to the pager network includes not only the critical event information just described, but also a personal identification number ("PIN") for the particular remote pager to which the message is to be sent.

As indicated by the fourth block 17 of FIG. 1, the preferred pager network is a network known as the "Star-Link" system, and provides automatic alphanumeric paging under the control of a computerized paging system. In fact, users of this type of paging network typically receive computer software that allows one, a nurse for example, to type an alphanumeric message into a computer system via a keyboard, which then employs special software to transmit this alphanumeric message to the paging network via the modem 23. In the preferred embodiment, formulation of an alphanumeric message and obtainment of a PIN is automatically performed by software running on the server workstation, any time a critical event is detected, without human intervention. It thus helps eliminate human error and time delays incurred in first noticing critical events in a patient's condition, and then, in notifying the physician who is responsible for the patient's care. Once the message is transmitted to the paging network, a transmitter 25 is used to send out the alphanumeric message, via satellite, such that it may be addressed to a particular PIN.

The fifth block 19 of FIG. 1, located at the bottom-middle of FIG. 1, shows an actual remote alphanumeric "beeper," or pager 27, which is preferably a commercially-available pager known as a "Palmtop" computer, and is also made by the Hewlett-Packard Company, model number 200LX. The pager is basically a notebook computer which includes a special circuit inserted into the side of the computer, namely a "StarLink" receiver circuit 29. This circuit includes radio frequency ("rf") circuitry necessary to intercept and decode messages addressed to that particular remote pager, as identified by the unique PIN associated with the receiver circuit 29.

Finally, the sixth block 21 of FIG. 1 illustrates an alphanumeric display screen of the "Palmtop" device 27, which can simultaneously display numerous lines of text. In particular, the "Palmtop" device 27 is carried by each physician that is to be reached using the preferred embodiment. When the physician is paged, the display screen 31 indicates the patient's name, the particular critical event which triggered the page, the patient's diagnosis, and the number and name of a nurse to whom the physician can convey responsive orders. [FIG. 1 does not show display of this latter information].

It is presently contemplated that this system will also provide for two-way communication, such that using the keyboard 33 of the "Palmtop" device 27, the physician can issue orders which are then transmitted in the reverse direction, e.g., to a paging or cellular radio network, via modem, page or radio link to the clinical information system, and to the pertinent workstation where the orders can be displayed to the nurse responsible for the patient.

As can be seen from FIG. 1, the preferred embodiment is a medical system that uses automatic review of both continuous and periodic electronic data representing a patient to automatically and immediately notice and report critical events. Contact is automatically made to a remote pager 27 by the preferred embodiment, such that a physician is immediately informed of the existence and the precise nature of the critical event. Thus, the physician can determine the seriousness of the critical event and how to appropriately respond to it.

With the principal parts of the preferred embodiment thus introduced, the design of the preferred system will now be described in further detail.

Figure 2:
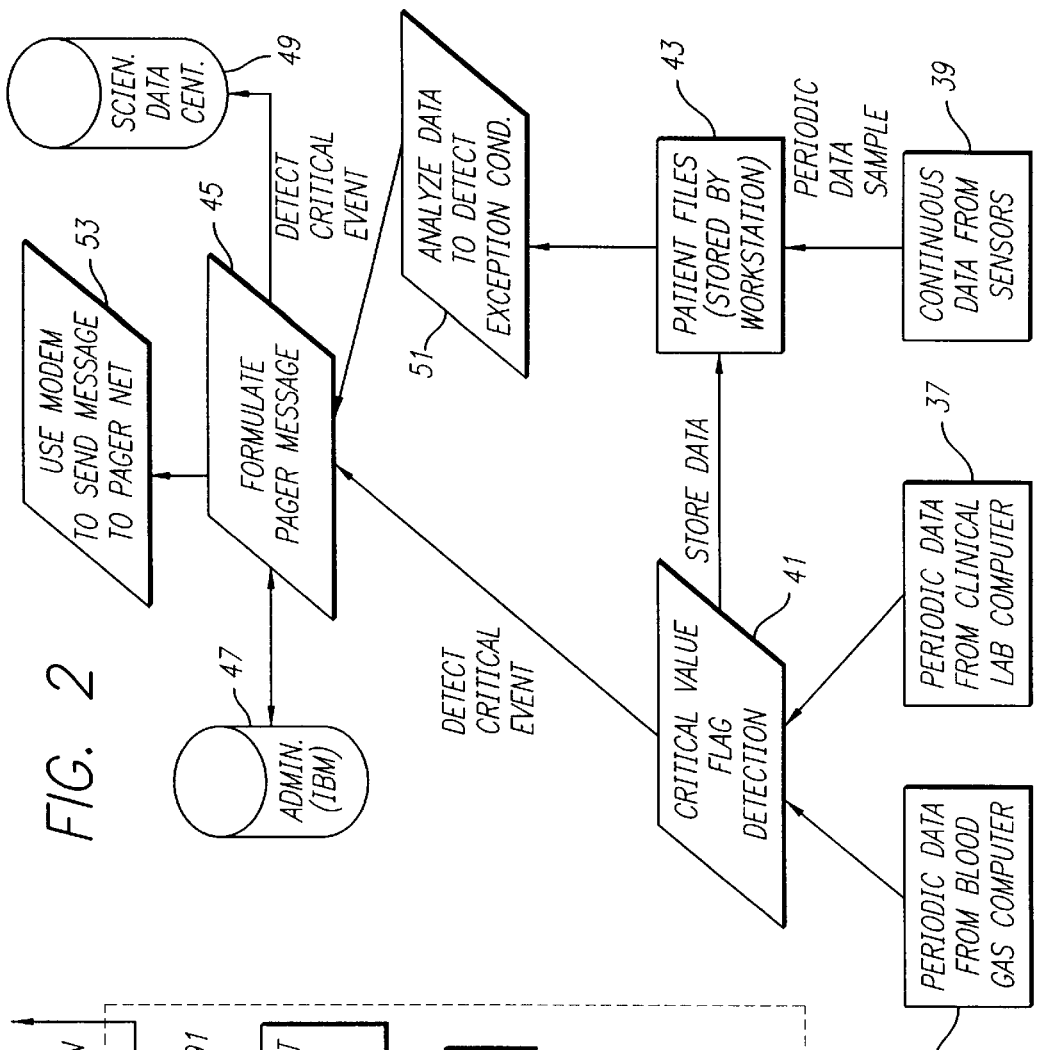
FIG. 2 is a block diagram showing the flow of data and decision making processes of the preferred embodiment. The bottom of FIG. 2 shows raw data, which is automatically processed to result in selective paging, as indicated at the top of FIG. 2; rectangles are used to represent data and hardware, parallelograms to represent actions and decision making activities, and cylinders to represent databases outside of the clinical information system.

II. FIG. 2; The Processing Of Patient Data

FIG. 2 helps further illustrate the operation of the preferred system. Patient data for each patient is provided to the clinical information system from three sources: These include (a) periodic data representing test results from a blood gas computer; (b) periodic data representing test results from a clinical lab computer; and, (c) continuous data provided directly to one of the workstations from a variety of sensors. These sources are respectively indicated as rectangular blocks 35, 37 and 39 at the bottom of FIG. 2.

Each of the blood gas computer and the clinical lab computer are autonomous computer systems which are completely separate from the "CareVue 9000" clinical information system and the workstations. They each include export utilities which automatically send any new data to the server workstation, which performs critical value flag detection, as indicated by the reference numeral 41. This data is then distributed to the particular workstation associated with the patient corresponding to the data, which stores this information a part of the patient's chart, or file. This latter operation is designated by the reference numeral 43.

In the preferred embodiment, data from the two periodic sources is electronically and automatically obtained, but is first reviewed by an assistant in the particular lab who can add notes or a critical flag to a patient file. The assistant then causes this data to be stored, in a storage device dedicated to the particular computer system, and the export utilities for the particular computer automatically send this data in a standard format, preferably the format known as "HL7". Table 1, below, provides an example of the "HL7" format.

TABLE 1

"HL7" Message Format

MSH|^~\&|CLI|SUNQUEST|CLI|8SICU|199506121204340||
    ORU^R01|118|P|2.1||^M
PID||000314643||DOE^JOHN||19230501|M|||||||||^M
OBR||L907569||||199506121100|||||||199506121122
    |||||||||F||||M74281|||||||^M
OBX|1|ST|CA^CALCIUM|1|5.5|MG/DL|8.3–10.7|L|||F|^M
NTE|||CRITICAL VALUE^M
OBX|3|ST|PHOS^PHOSPHORUS|2|3.7|MG/DL|2.5–5.0||||F|^M
OBX|4|ST|URCA^URIC ACID|3|5.2|MG/DL|2.8–8.0||||F^M
OBX|5|ST|TBIL^BILIRUBIN, TOTAL|4|.05|MG/DL|0.1–1.2||||F|^M
OBX|6|ST|DBIL^BILIRUBIN, DIRECT|5|TOTAL B|MG/DL|<0.3||||F|^M
NTE|||NOT CALCULATED^M
OBX|8|ST|TP^PROTEIN, TOTAL|7|4.5|G/DL|6.0–8.5|A|||F|^M
OBX|9|ST|ALB^ALBUMIN|8|2.7|G/DL|3.5–5.5|A|||F|^M
OBX|10|ST|ALP^ALKALINE PHOSPHATASE|9|44|U/L|<108||||F|^M
OBX|11|ST|AST^ASPARTATE AMINOTRANS [SGOT]|10|55|U/L|<35
    |A|||F|^M
OBX|12|ST|ALT^ALANINE AMINOTRANS [SGPT]|11|23|U/L|<40||||
    F|^M
OBX|13|ST|MG^MAGNESIUM|12|1.6|MG/DL|1.6–2.6||||F|^M

In the fourth line of Table 1, above, the parameter |L| represents a critical event associated with a low calcium reading, as determined in the blood gas chemistry lab. This flag in the preferred embodiment is added by the assistant who monitors a display of the electronically-ascertained data; the software used by the particular computer system is used to automatically detect a critical value and bring it to the attention of the assistant, for example, using highlighting in the visual display. Upon noticing a critical value, the human assistant further utilizes the software to cause a critical flag to be attached to the record, as well as the note reflecting the existence of the critical value. Receiving this message, the workstation server simply monitors the "HL7" format to detect occurrence of the parameter |L|, by comparing each data transmission of the message with this quantity. Further desired critical event parameters, and comparison characteristics that have actually been implemented, are indicated in tables 2 and 3, below.

TABLE 2

Critical Event Parameters

| Serum Chemistries | Drug levels |
|---|---|
| Sodium | Phenytoin |
| Potassium | Theophylline |
| Chloride | Phenobarbital |
| Bicarbonate | Quinidine |
| Calcium | Lidocaine |
| Hematology | Procainamide |
| Hemoglobin | NAPA |
| Hematocrit | Digoxin |
| White Blood Count | Thiocyanate |
| Partial Thromboplastin Time | Gentamicin |
| Prothrombin Time % Activity | Tobramycin |
| Arterial blood gas | Cardiac Enzymes |
| pH | Creatinine kinase (CK) |
| $PO_2$ | CK-MB |
| $PCO_2$ | |

TABLE 3

Critical Event Parameters And Comparison Values

| | Low | High |
|---|---|---|
| Na+ | 120 | 160 |
| K+ | 3.0 | 6.5 |
| Cl− | 80 | 156 |
| $HCO_3$ | 10 | 40 |
| Hgb | 7 | 18 |
| Hct | 21 | 60 |
| WBC | 2 | 35 |

Critical event detection can also be accomplished by programming the server workstation with alerting algorithms that look at the numerical value of each parameter to compare it to an associated number, instead of comparing the quantities in the "HL7" format with the alphanumeric quantity |L|. In this latter example, there would be no need for the lab assistant to insert a critical event flag into the "HL7" format message, but the critical event would be directly determined using numerical data within the "HL7" format message. In fact, automated review of this nature is implemented for determination of some exception conditions, e.g., some exception condition review is automatically triggered upon arrival of certain new data, such as from a ventilator. It is well within the skill of one familiar with computer systems to construct an alerting algorithm of this type.

Irrespective of the manner in which a critical event is determined to exist, the clinical information system both stores the periodic information in the patient's file, and also proceeds to formulate a pager message, as indicated by a middle block 45 of FIG. 2, where parallelograms are used to represent actions taken by the clinical information system. During the formulation of a pager message, the system requests the identity of a physician PIN and the name of a nurse and corresponding telephone number from administrative files stored by an external, administrative computer 47. This administrative computer maintains a database of this information, and returns appropriate information depending upon staffing, for example, depending upon time of day, shift, etc. It automatically selects each appropriate physician PIN, a name of a responsible nurse whom the physician(s) may call in response to the page, and a telephone number. In requesting this information, the clinical information system provides an identity (number or name) for the particular patient, to be used by the administrative computer as an index. The administrative computer 47 returns this requested information to the clinical information system, which then inserts the requested information into the pager message and exports the PIN for each physician to be paged. Each PIN is used by the paging network as an address to which the alphanumeric message will be sent.

At this same time, the clinical information system also sends the pager message to a pager message database log 50, which stores the pager message as a record of the critical event, for use in records, statistics and review of system performance.

As to patient data from the third source 39, continuous data from the patient's bedside is directly provided to a particular workstation of the clinical information system by means of electronic sensors, such as heart rate sensors, IV monitors and the like. The software running on the clinical information system permits a nurse or technician to automatically sample and store this information as part of the patient's chart when readings are representative of the patient's condition. Typically, this will be done each hour for ICU patients, but it may be done at any desired time or time interval.

As indicated by the block 43 of FIG. 2, the particular workstation dedicated to each patient displays both the just-mentioned samples of the continuous data, and also new lab data sent to it from the server workstation, as part of the patients' files. These files are periodically stored in a mass storage device, which act as a data archives.

Periodically, alerting algorithms are employed by the workstation to determine the existence of an "exception" condition, an operation indicated by the parallelogram 51. The term "exception condition" refers to complex conditions that can be ascertained by a review of different data, representing the same or different parameters. As examples, one exception condition used in connection with a patient on a ventilator is whether the patient has required levels of oxygen ventilation of greater than 60% oxygen composition for over four hours duration. This type of condition cannot in the preferred embodiment be determined from just instantaneous data provided from directly from the ventilator, and so, patient files are periodically reviewed to look at several, time-spanned data entries representing oxygen composition. In fact, as mentioned, review of this data is triggered anytime new data is received. For example, if continuous data provided from the ventilator to the particular workstation has been sampled once each hour, then as each new data is received, the four most-recent ventilator data samples may be examined each hour to determine whether the exception conditions have been met (in the preferred embodiment, ventilator data is updated as often as once per minute). Other exception conditions may be based on a combination of different types of data, for example, an exception condition detecting a pathological arrhythmia could be based upon both instantaneous heart rate and respiration rate. Exception conditions used in the preferred embodiment are identified in table 4, below.

TABLE 4

Exception Conditions $FiO_2$ > 60% for 4 hours or more
Urine output < 0.3 cc/kg/hr and
    patient not admitted in renal failure
Pulmonary capillary wedge pressure > 22 mm Hg
Systolic blood pressure < 80 mm Hg and
    patient has no pulmonary artery catheter
Systolic blood pressure < 80 mm Hg and
    pulmonary artery wedge pressure < 10 mm Hg
Ventricular tachycardia (cardiac arrhythmia)
Ventricular fibrillation (cardiac arrhythmia)
Code Blue (cardiac arrest)
PEEP > 15 cm $H_2O$
Readmission to SICU < 48 hours after discharge Critical events in the preferred embodiment are ascertained using the alerting algorithms by (1) detection of a critical value flag in a "HL7" format message or (2) via detection of an exception condition. These operations are expressed as the parallelograms 41 and 51 found in roughly the middle of FIG. 2. Once a critical event is detected, software run by the server workstation is used to compile an alphanumeric pager message (as indicated by the parallelogram 45) and obtain a PIN for each physician to whom the message is to be sent. Once the message is formulated, it along with each physician PIN is sent to the "Starlink" paging network via modem, which causes the physician(s) to be paged and the alphanumeric message to be transmitted to them. This operation is designated by the reference numeral 53 of FIG. 2.

Examples of physicians' remote beeper display of alphanumeric messages for each type of critical event (exception condition and critical value) are seen in FIGS. 10 and 11, respectively. In particular, these figures show use of the Hewlett-Packard model 200LX Personal Data Assistant, which has a multi-line alphanumeric display and a PCMCIA receiver fitted to the unit. One new system that shows promise for use in the future is the new M1490A Palmtop System, also available from Hewlett-Packard, which uses "PalmVue" software. This latter system has capabilities that allows it to display graphs and charts and the like, as part of the alphanumeric display.

III. Hardware Of The Preferred Embodiment

Figure 4:
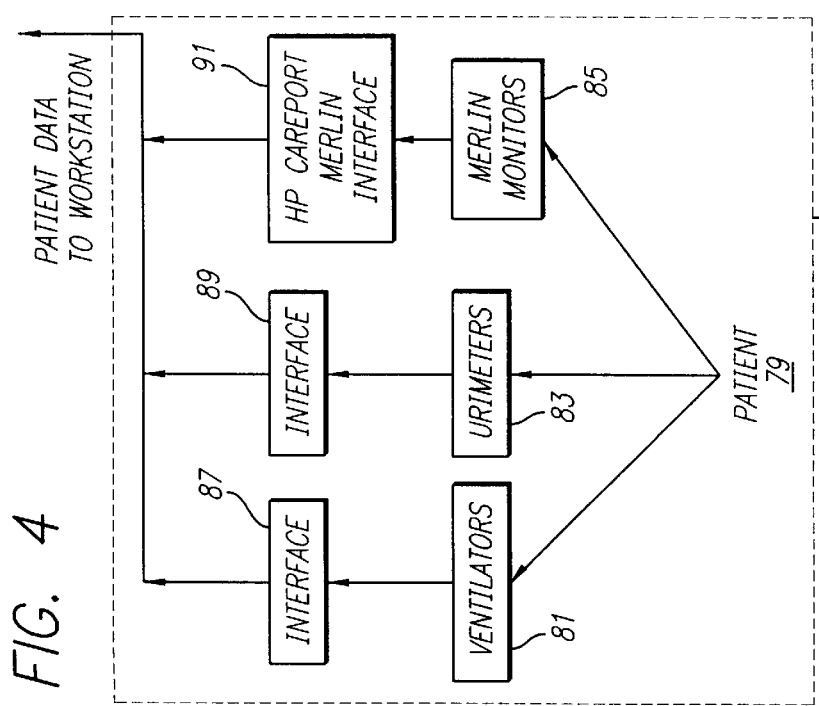
FIG. 4 illustrates the patient data blocks of FIG. 3 in greater detail; in particular, it illustrates hardware that is preferably used to monitor Intensive Care Unit ("ICU") patients and provide a source of continuous patient data to the clinical information system.

FIGS. 3 and 4 help illustrate the hardware of the preferred embodiment. FIG. 3 shows an overview of the entire system 55, whereas FIG. 4 shows the constituency of one of the "patient data" blocks 57 input to each workstation 59, as indicated in phantom in FIG. 3.

Two different groups of computer systems 61 and 63 are seen in FIG. 3. First, the clinical information system 61 is seen at the right side of FIG. 3, and consists of multiple workstations 59 connected by a local area network 67, each workstation receiving continuous patient data as distributed by a server workstation 69. The server workstation 69 interfaces with external hospital computer systems (designated 63) and databases, which are seen at the left-hand side of FIG. 3. They include (1) a blood gas lab computer 71, which is preferably a Digital Equipment Corporation ("DEC") model 11/23 computer system; and (2) a clinical lab computer 73, which is preferably a VAX model 8530 computer system. Each of these computer systems, as alluded to earlier, maintains its own database and memory, and uses scripting to export any new patient data to the clinical information system 61 as that data is stored on that system. Those desiring additional detail as to the interface between these computer systems 71 or 73 and the clinical information system 61, and how new data from these computer systems is processed, are referred to the following references: (1) "Inferencing Strategies For Automated Alerts On Critically Abnormal Laboratory And Blood Gas Data" by authors Shabot, LoBue, Leyerle and Dubin, *Proceedings Of The Thirteenth Annual Symposium On Computer Applications In Medical Care*, Washington, D.C., Nov. 5–8, 1989; (2) "Real-Time Wireless Decision Support Alerts on a Palmtop PDA," by M. Shabot and M. LoBue, *Nineteenth Annual Symposium On Computer Applications In Medical Care*; and also (3) *Decision Support Systems In Critical Care*, Ed. M. Michael Shabot and Reed Gardner (Springer-Verlag 1994). These references are hereby incorporated by reference into this disclosure, as though fully set forth herein.

In addition to these computer systems, the external hospital computer systems also include (3) the scientific data center computer 49, which consists of a VAX cluster, and (4) the administrative computer 47, which is preferably an IBM mainframe. All four of these computer systems 47, 49, 71 and 73 are coupled to the server workstation 69 via a second local area network 75, which is different than the network 67 for the clinical information system. Lastly, the server workstation also interfaces with a mass storage device 77 (labelled "data archives" in FIG. 3), used for storage of patient files, and the internal modem 23 which is used to report critical events to the pager network and page physicians. Many suitable modem and mass storage devices are available and appropriate, and selection of one is left to one of ordinary skill with computers.

FIG. 4 helps show the constituency of each "patient data" block 57 of FIG. 3. The patients 79 are monitored by three different devices, including ventilators 81, urimeters 83 and Merlin monitors 85. The ventilators 81 can be any commercially-available ventilators, which will supply numerous types of information updates to the clinical information system, for example, consisting of many different parameters, each time there is any type of change in any one of them. Since the format of this data and its transmission does not necessarily match the format accepted by the CareVue 9000 system, a digital interface 87 is constructed to adapt the transmission of information from the ventilators 81 to a uniform format that is placed upon a third network 93 that is coupled to the server workstation 69. Likewise, data from urimeters 83 must also pass through an interface 89 to place information on the network. Finally, the Merlin monitors 85 directly monitor IV sensors and life sign sensors, and provide this data through a HP Careport Merlin interface 91 onto the network 93. This latter interface is chosen to be a model 1000/A600, also available from the Hewlett-Packard company. With these interfaces 87, 89 and 91, data changes may be reported to the clinical information system 61 which may then sample the data to display current patient readings; the clinical information system is used to selectively sample these readings and write them to a permanent file, i.e., the patient's chart.

IV. Software Of The Preferred Embodiment

FIGS. 5–9 show functional blocks which correspond to the parallelograms 41, 45, 51 and 53 seen in FIG. 2. FIGS.

5 and 6 in particular show functional block diagrams for detecting alerting triggers, based on critical value flags, and detection of exception conditions, respectively. FIG. 7 shows the formulation of a pager message, whereas FIGS. 8 and 9 together show the queuing and sending of pager messages under modem control, respectively. All of the software to effectuate these functions is written in C++ and is principally run on the server workstation 69.

Figure 5:
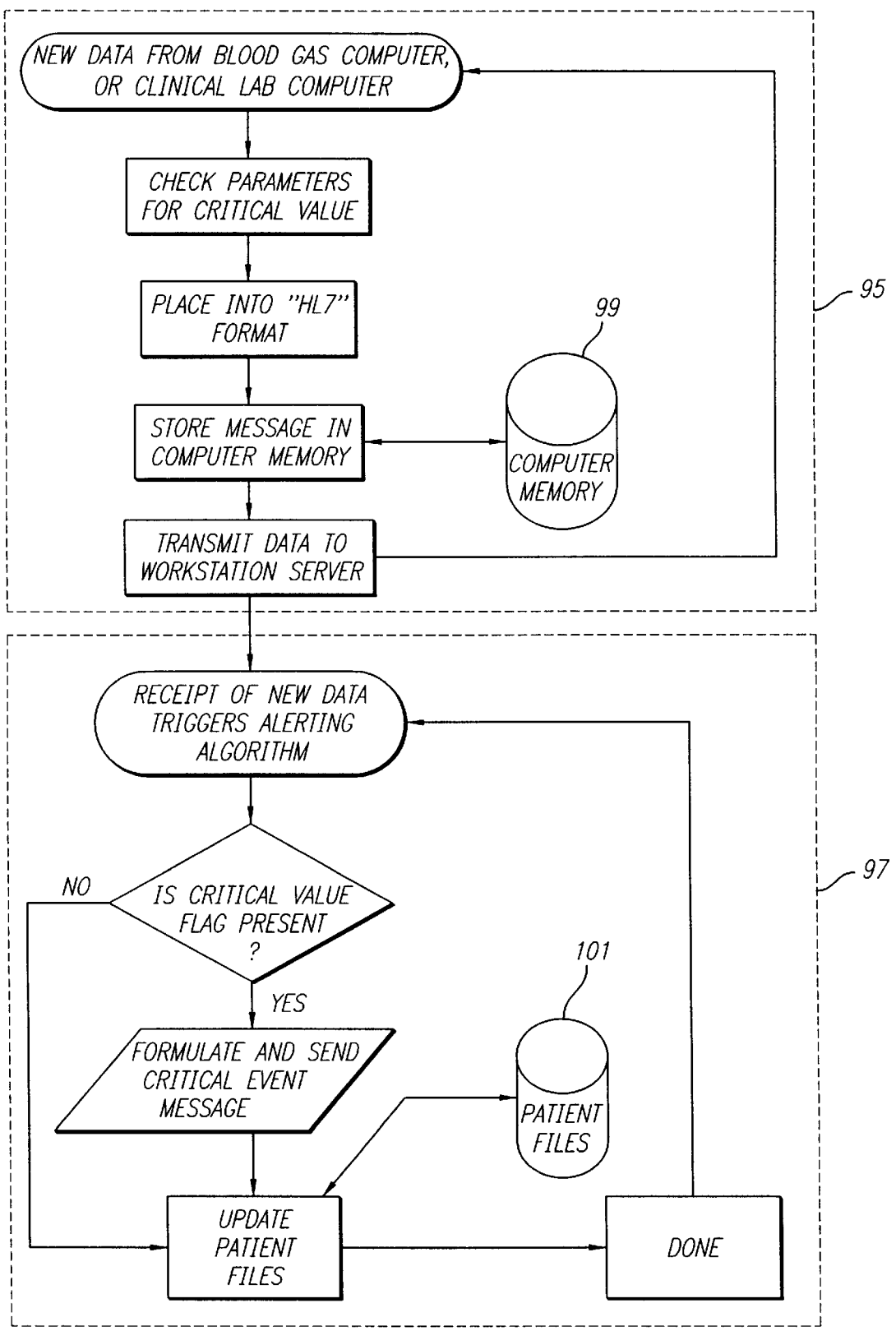
FIG. 5 illustrates in greater detail the operations associated with the parallelogram labelled "Critical Value Flag Detection" of FIG. 2.

FIG. 5 has two general sections 95 and 97 which are illustrated in phantom; the first section 95 refers to activities of the external computer systems (either the blood gas computer 71 or the clinical lab computer 73), whereas the second section 97 shows activities performed by the clinical information system 61 as data from these computers is received and distributed. As indicated by the top section 95 of FIG. 5, scripting is used to generate a data record each time new data is received; this information is both written to the computer system's memory 99, and also placed into "HL7" format. At this time, scripting of the particular computer 71 or 73 is written so as to preferably detect and highlight the display of critical values. A lab technician also visually reviews the data as it appears to him on a monitor, to attach specific notes and flags, including critical value flags as appropriate. The message is then placed into the "HL7" format, and is stored in the memory 99 of the computer. The scripting for the computer 71 or 73 also copies this message and send it to the clinical information system 61.

The clinical information system 61 of the preferred embodiment analyzes each new data message from either the blood gas computer 71 or the clinical lab computer 73 to determine whether the message contains a critical event flag, i.e., the quantity |L| if the message is "HL7" format. Accordingly, the server workstation 69 first determines whether this quantity is present, and if so, formulates a critical event message and causes it to be sent to the paging network. However, whether or not this quantity is present, the clinical information system 61 updates patient files 101 (i.e., the particular patient's chart stored in the data archives 77) to reflect the new data.

FIG. 6 is a block diagram of one alerting algorithm that reviews exception conditions. In general, each exception condition has a dedicated algorithm that is run on a periodic basis, for example, each hour, or each time certain new data is received. When an algorithm is called, it extracts parameters as needed sequentially from each patient file 101 in the data archives 97, that is, from each patient file maintained by the server workstation. These parameters are compared to predetermined alphanumeric quantities, to ascertain whether they bear a predefined relation to those quantities. For example, using one example stated above relating to ventilators, an alerting algorithm retrieves each oxygen sample from the patient files for the previous four hours duration; with respect to each sample, the algorithm compares the sample with a quantity representing sixty percent oxygen. If all of the samples satisfy the relation that they are greater than this figure, a critical event is detected, and a specific message is formulated relating to the critical event. For example, the pager message seen in FIG. 10 represents two simultaneous critical events, including a ventilator oxygen component of greater than four hours, and a PEEP value that is greater than or equal to fifteen. The comparison quantities do not have to be numeric but, for example, may also be or include alphabetical or other quantities.

FIG. 7 shows a functional diagram for the processing of detected critical events and message formulation. When a critical event is detected, the clinical information system 61 sends a patient identifier (a number corresponding to the particular patient, or to the particular hospital bed) to the administrative computer 47, and requests a physician PIN for each physician to be paged in response to detection of a critical event. For example, a critical event corresponding to an ICU patient might require paging of a resident and an attending physician. The administrative computer 47 stores information on physicians responsible for each patient's care, and returns the requested information to the clinical information system 61 for use in connection with paging. Additionally, however, the administrative computer 47 also stores information regarding the nurse to be contacted for the particular patient and the telephone number by which the physician(s) paged can contact the nurse to deliver orders in response to the page. This information is also returned to the clinical information system 61 by the administrative computer 47, for incorporation into the critical event message. Finally, one contemplated embodiment also sends an indication of the particular critical event to the administrative computer, in order that a specialist may be also paged. For example, if the particular critical event is the ventricular fibrillation exception condition, the clinical information system 61 may indicate to the administrative computer 47 that the physician PIN for a cardiologist on-call should also be returned to the clinical information system together with the other information. In this manner, an alphanumeric message is formulated for each PIN of a physician to be paged, and may consist of the following information: (1) critical event number; (2) type of critical event—either an exception condition or a critical (alert) value; (3) patient name; (4) patient number; (5) patient diagnosis; (6) patient location (e.g., ICU); (7) patient age; (8) date and time; and (9) other patient data, such as length of time that the patient has been in ICU, for example. All of this information is retrieved from the patient file by the clinical information system at the time that a critical event is detected. In addition to this information, the critical event detection algorithms also return to the message formulation routine information as to the (10) exact type of critical event (e.g., low blood pH level) that has been detected and (11) precise values that triggered detection the critical event (e.g., pH of 6.99).

Finally, information maintained in databases stored in the external computer systems, namely, in the administrative computer system, is requested and provided to the clinical information system as just described. This information includes (12) physician PIN(s) for paging each physician responsible for the patient, (13) a nurse name and (14) a nurse telephone number. The physician PIN(s) are used to determine the number of messages that will be sent to the Starlink paging system, one copy addressed to each physician to be paged. The latter information is included in the alphanumeric message sent to each physician if the system is configured to monitor patients in diverse locations, e.g., it would be difficult to phone orders in without it.

Figure 8:
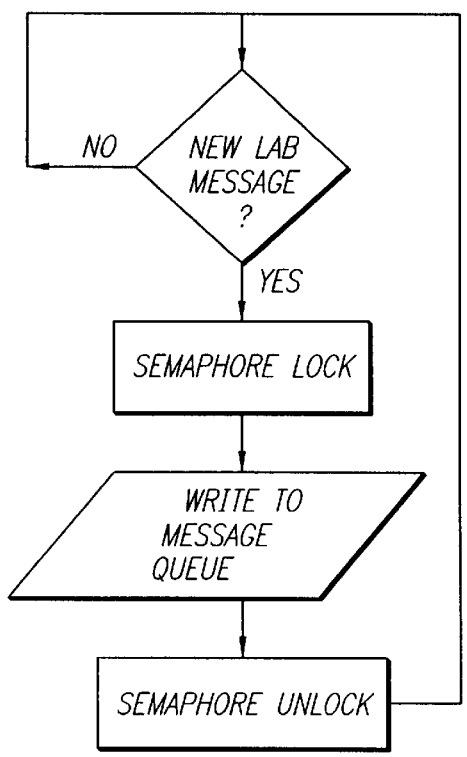
FIG. 8 illustrates one of two routines that implement the parallelogram labelled "Used Modem To Send Message To Pager Net." of FIG. 2; in particular.
Figure 9:
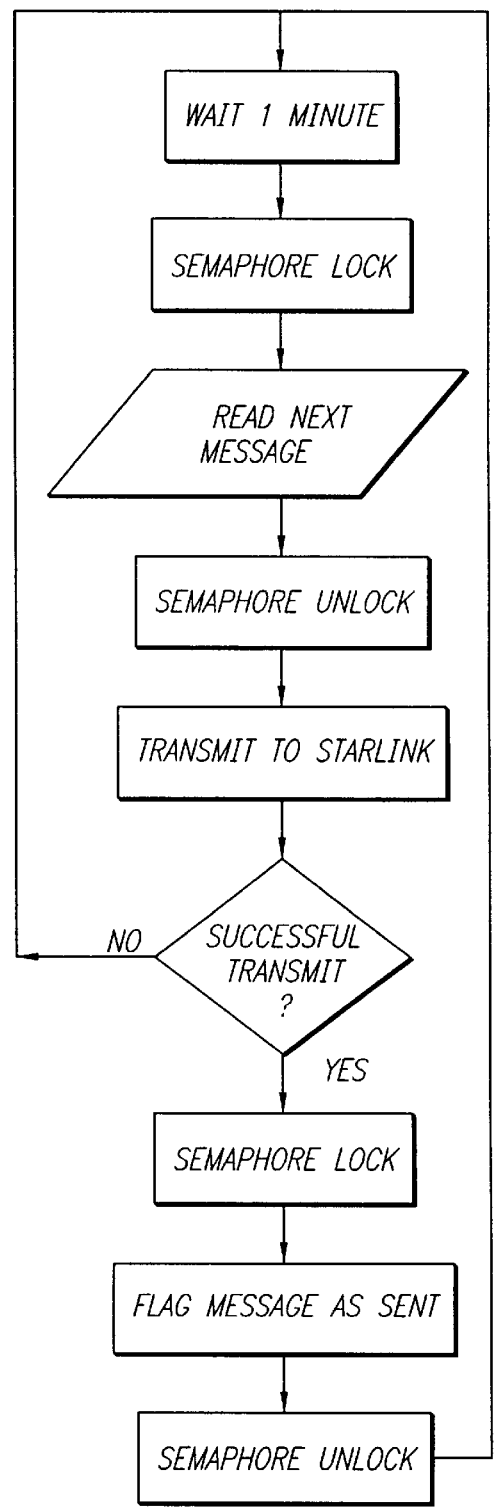
FIG. 9 illustrates a second of two routines that implement the parallelogram labelled "Used Modem To Send Message To Pager Net." of FIG. 2; in particular.

FIGS. 8 and 9 show the placing of alphanumeric messages into a queue for transmittal to the Starlink paging network. As indicated by FIGS. 8 and 9, each time a critical message is generated, it is placed into a queue of messages awaiting modem transmission. This implementation is preferred, because in a typical case, more than one physician will be paged, hence multiple messages can be generated by the clinical information system in a very short time period. An independent routine, as indicated by FIG. 9, retrieves messages from the queue and transmits them to the Starlink paging network via modem, and flags the message as having been sent.

Use of a unique PIN for each physician permits messages to be independently directed to each physician. The Starlink network is effective, upon receiving a modem transmission containing a PIN and an alphanumeric message, to page the particular physician corresponding to the PIN and to display upon the remote beeper (the HP 200LX Personal Data Assistant) the precise alphanumeric message that was formulated by the software of the server workstation. Two examples of alphanumeric messages sent using the Starlink paging network are seen in FIGS. 10 and 11, as they would appear upon the 200LX remote beeper's display screen.

Numerous prospective improvements to this preferred embodiment are contemplated to be within the scope of the present invention, as it is defined in the claims below. First, particular medical conditions have been chosen for critical event analysis in the preferred embodiment; it should be apparent that any type of medical condition may be programmed for critical event analysis. For example, the HP CareVue 9000 system can permit review of hundreds of parameters; a flowsheet showing some of these parameters reviewed by the clinical information system is seen in FIGS. 12 and 13. The clinical information system can be programmed to detect nearly any condition or combination of conditions, instantaneous, time-distributed, or otherwise, as is believed to be appropriate. As another example of a prospective embodiment, the new "PalmVue" model M1490A system from Hewlett-Packard permits not only display of alphanumeric pager messages, but also graphical displays showing cardiographs and other types of information, as part of the pager message. It would be well within the skill of one familiar with hospital computer systems to implement pager messages that include waveforms, for example, cardiographs, as well as to implement waveform analysis as a critical event detection mechanism. Also, as mentioned, it is contemplated that alphanumeric display devices also include a keyboard 33, which can be used to automatically transmit orders and other information back to the hospital, so that the physician does not require access to a telephone. Finally, the present invention is not limited to applications dealing with medicine or hospital care.

Having thus described an exemplary embodiment of the invention, it will be apparent that further alterations, modifications, and improvements will also occur to those skilled in the art. Further, it will be apparent that the present invention is not limited to use of a medical paging apparatus. Such alterations, modifications, and improvements, though not expressly described or mentioned above, are nonetheless intended and implied to be within the spirit and scope of the invention. Accordingly, the foregoing discussion is intended to be illustrative only; the invention is limited and defined only by the various following claims and equivalents thereto.

We claim:

1. An automatic critical event notification system, comprising:

a remote pager having a display screen and an identification number;

a paging system that selectively transmits a message to the remote pager using the identification number, to cause the remote pager to display the message;

data representing variable values of a parameter; and a computer system electronically coupled to the paging system that is configured to unsolicitedly by not receiving instruction from the remote pager, automatically receive the data and determine whether the values of the parameter have a predetermined relation with respect to a predefined quantity, automatically formulate a particular message that indicates the existence of the relation, in response to the determination that values of the parameter satisfy the relations and automatically send the particular message to the paging system in electronic format, together with the identification number for the remote device;

wherein the paging system automatically pages the particular remote pager identified by the identification number and sends to it the particular message indicating the existence of the relation.

2. A system according to claim 1, wherein:

the data represents values of a patient statistic;

the predefined quantity is a value of the statistic that represents a change in the condition of the patient for which it is appropriate to notify a physician; and the predetermined relation represents values of the patient statistic which are one of greater than, less than and equal to the predefined quantity.

3. A system according to claims 1 or 2, wherein:

the system further comprises data for each one of a plurality of different parameters;

the predetermined relation is satisfied only when data for each one of the plurality of different parameters meets a predefined condition; and the computer system is configured to, with respect to each one of the plurality of different parameters, compare data representing the corresponding one of the parameters with a corresponding predefined quantity, to determine whether the predetermined relation is satisfied.

4. A system according to claims 1 or 2, wherein:

the system further comprises a plurality of data inputs, each corresponding to a different medical patient, the data inputs each representing measurement of the same patient statistic;

the computer system includes a table that indicates a responsible user for each patient and a unique identification number for a remote pager corresponding to each user;

the computer system is configured to determine whether the relation exists for each of the plurality of data inputs;

identify, responsive to a determination that the relation exists for a particular patient, a particular identification number that corresponds to the pager of a user corresponding to the particular patient; and automatically, without receipt of instruction from a pager of a user, formulate and send the alphanumeric message to the user corresponding to the particular patient, via the paging network.

5. An automatic critical event notification system, comprising:

detection means for unsolicitedly and electronically comparing data having variable values with at least one predefined quantity, to determine the existence of a predetermined relation;

message means for formulating an alphanumeric message that indicates the predetermined state, in response to the existence of the predetermined relation; and remote transmission means for transmitting the alphanumeric message to the remote message receiving device in response to the existence of the predetermined relation;

wherein the predetermined relation is automatically detected from the data and the alphanumeric message is automatically, without receipt of instruction from a remote message receiving device, and electronically formulated and transmitted to the remote message receiving device.

6. A system according to claim 5, wherein: the detection means includes multiple parameter means for receiving a plurality of data inputs, each representing a different parameter, and for determining and distinguishing each one of a plurality of predetermined relations, each relation corresponding to a condition relative to one or more parameters represented by the data inputs;

the message means includes multiple message means for formulating a different alphanumeric message for each predetermined relation in response to detection of such relation by the detection means; and the remote transmission means receives each alphanumeric message formulated by the multiple message means and includes sending means for sending each alphanumeric message to the remote receiving device;

wherein each predetermined relation is automatically detected from the plurality of data inputs and a corresponding alphanumeric messages is automatically and electronically formulated and transmitted to the remote message receiving device.

7. A system according to claims 5 or 6, wherein:

the system further comprises addressing means for selecting one of a plurality of remote receiving devices that is to receive the alphanumeric message generated by the message means; and the remote transmission means is responsively coupled to the addressing means to automatically send the alphanumeric message to a selected one of the remote receiving devices.

8. An automatic critical event notification system used to notify at least one of a plurality of users as to a critical event representative of the condition of at least one of a plurality of patients, comprising:

a remote pager carried by each user, each remote pager having an alphanumeric display and a unique personal identification number;

a pager network adapted to receive a message and a pager number sent via a communication device, the pager network responsive to selectively send the message to a particular remote pager identified by the pager number;

a database that receives electronic data representing each patient's condition;

a computer system having a communication device, wherein the computer system, is configured to unsolicitedly, by not receiving instruction from the remote pager carried by each user, and automatically monitor the database with respect to each one of the plurality of patients, to detect whether the data for represents a critical event and responsively indicate a detected critical event, formulate an alphanumeric message indicating the existence of the detected critical event, determine a user responsible for the care of the patient corresponding to the detected critical event and identify the particular personal identification number which corresponds to that user, and control the communication device of the computer system to establish an electronic link with the pager network and send the particular personal identification number to the pager network as the pager number, and send the alphanumeric message to the pager network;

wherein the pager network is automatically responsive to the computer system to send the alphanumeric message to the remote pager of the user responsible for the care of the particular patient, and the alphanumeric display of the pager displays the alphanumeric message to thereby indicate the existence of the predetermined relation, thereby notifying the user of the predetermined relation without requiring a real-time human decision to page the user.

9. A system according to claim 8, wherein one of a plurality of nurses is also responsible for the care of each patient, and each nurse may be reached using a telephone number, and wherein:

said system further comprises a table of names of nurses and corresponding telephone number, indexed by patient;

the computer system is further configured to determine from the table a particular nurse responsible for the care of the particular patient and identify the telephone number by which the particular nurse may be reached, and formulate the alphanumeric message to include the name of the particular nurse and the telephone number by which the particular nurse may be reached; and the alphanumeric display of the pager is caused to display the name of the particular nurse and the telephone number by which the particular nurse may be reached.

10. A system according to claims 8 or 9, wherein the alphanumeric message is formulated to includes the name of the particular patient.

11. A system according to claims 8 or 9, wherein the alphanumeric message is formulated to includes a prior diagnosis of a medical condition of the particular patient.

12. A system according to claims 8 or 9, wherein:

the computer system uses at least one table that stores the personal identification number of each user, the name of each nurse and corresponding telephone number by which the nurse nay be reached, and utilizes an index that permits a determination by the computer system of the identities of the personal identification number of the user and of the name of the nurse responsible for the care of the particular patient, as well as a telephone number by which the nurse may be reached; and the computer system is configured to access the table to formulate the alphanumeric message and cause the paging of the user responsible for the care of the particular patient.

13. A system according to claims 1, 5 or 8, wherein:

the predetermined relation also includes the relation of averaged data being one of less than, greater than, and equal to the predefined quantity; and the computer system includes a memory and software that causes it to store the data in the memory, periodically interrogate the memory to average the data samples to thereby produce the averaged data, and compare the averaged data with the predefined quantity to detect the existence of the predetermined relation.

14. A system according to claims 1, 5 or 8, further comprising a sensor that generates the data as a data stream representing measurement of a physiological parameter made by the sensor.

15. A system according to claim 14, wherein the sensor is one of a blood gas sensor, a urimeter, a respirator, a heartbeat detector and an integrated medical station having at least one input which is periodically sampled by the integrated medical station.

16. A system according to claims 1, 5 or 8, wherein the data is formatted in a HL7 standard.

17. A system according to claims 1, 5 or 8, wherein the computer system includes at least two stand alone computers, and wherein:

the predefined quantity is a predefined value of critical event flag and the predetermined relation includes equality between selected data and the predefined value of the critical event flag;

a first stand alone computer (a) receives a data stream from each of a plurality of sensors, (b) adds to those data streams the critical event flag, to indicate the occurrence of a critical event, and (c) sends those data steams with the critical event flag to a second stand alone computer; and the second stand alone computer includes a flag detection mechanism, the flag detection mechanism comparing the data streams received from the first stand alone computer with a predetermined quantity to detect an equality relation between the two, the computer system thereby determining that the predetermined relation exists.

18. A system according to claim 17, wherein:

the predetermined relation also includes a second relation of averaged data being one of less than, greater than, and equal to the predefined quantity; and the second stand alone computer includes a memory and software that causes the second stand alone computer to store the data streams received from the first stand alone computer in the memory, periodically interrogate the memory to average samples from one of the data streams, to thereby produce the averaged data, and compare the averaged data with the predefined quantity to detect the existence of the second relation.

19. A method of automatically notifying an individual of the existence of a critical value of a measurement parameter, using a computer system, a remote pager and a paging network, the computer system having a communications device that permits it to selectively communicate with the paging network, comprising:

using the computer system to automatically and unsolicitedly monitor data representing the measurement parameter by receiving that data with the computer system and automatically comparing the data with a predefined quantity to detect the existence of the critical value, thereby indicating the existence of a critical event;

in response to detection of the existence of the critical event and without receipt of instruction from the remote pager, causing the communications device to automatically establish a communications link between the paging network and the computer system; and using the computer to transmit a message to the paging network which causes the paging network to automatically notify the remote pager.

20. A method of automatically notifying an individual having a remote pager with alphanumeric display capabilities of the existence of a critical event, said method using a paging network that can receive instructions to page the remote pager and transmit to it an alphanumeric message, a source of data and a computer system that is electrically connected to the source of data, said method comprising:

using the computer system to automatically, unsolicitedly, by not receiving instructions from a remote pager, and electronically receive the data from the data source and automatically check the data to detect the existence of a critical value in the data, to thereby determine that the critical event has occurred;

upon detection of the critical value,
automatically formulating with the computer system an alphanumeric message indicating the existence of the critical event,
causing the computer system to automatically establish a communications link with the paging network,
causing the computer system to transmit the alphanumeric message to the paging network;

wherein the paging network upon receipt of the message automatically transmits the alphanumeric message to the remote pager, and said method automatically detects the critical event and causes the remote pager to display the alphanumeric message indicating the existence of the critical event without requiring a human decision to page the remote pager.

21. A method according to claims 19 or 20, wherein the measurement parameter represents a patient statistic, and wherein the computer system is coupled to an electronic sensor that electronically measures the patient statistic and produces the data, the method further comprising:

periodically sampling the electronic sensor with the computer system to produce a series of sequential data samples representing the patient statistic over time; and comparing the series of sequential data samples with the predefined quantity to determine the existence of the critical value.

22. A method according to claim 21, wherein comparing the series of sequential data samples includes calculating an average of selected samples within the series, and comparing the average to the predefined quantity.

23. A method according to claims 19 or 20 which monitors two different measurement parameters to detect the existence of the critical event, the method further comprising:

causing the computer system to compare data representing each of the measurement parameters with corresponding predefined quantities; and detecting the existence of the critical event only when data for each of the measurement parameters bears a predetermined relation to the corresponding predefined quantities.

24. A method according to claims 19 or 20, wherein said method further uses a plurality of remote pagers, each remote pager having a unique personal identification number associated with it, as well as a table that identifies a subset of the plurality of remote pagers (by at least personal identification number) that is to be notified upon the detection of the critical event, said method further comprising:

upon detection of the critical event, causing the computer system to interrogate the table and extract from it each unique personal identification number that corresponds to a remote pager that is to be notified of the critical event; and responsively causing the computer system to transmit to the paging network each personal identification number corresponding to a remote pager that is to be notified of the critical event;

wherein the paging network automatically pages each remote pager in the subset.

25. A method according to claim 24, wherein each pager includes an alphanumeric display and wherein:

the computer system is further used to generate an alphanumeric message that identifies the critical value of the parameter and its relation to the predefined quantity; and the paging network automatically sends the alphanumeric message to each remote pager in the subset.

* * * * *

UNITED STATES PATENT AND TRADEMARK OFFICE
CERTIFICATE OF CORRECTION

PATENT NO. : 5,942,986 C1
APPLICATION NO. : 90/009587
DATED : May 31, 2011
INVENTOR(S) : Shabot et al.

It is certified that error appears in the above-identified patent and that said Letters Patent is hereby corrected as shown below:

On the Title Page, Item (73) Assignee, please delete "Cedars-Sinaimedical Center" and insert
-- Cedars-Sinai Medical Center --.

Signed and Sealed this
Twelfth Day of July, 2011

David J. Kappos
*Director of the United States Patent and Trademark Office*

US005942986C1

(12) EX PARTE REEXAMINATION CERTIFICATE (8278th)
United States Patent
Shabot et al.

(10) Number: US 5,942,986 C1
(45) Certificate Issued: May 31, 2011

(54) SYSTEM AND METHOD FOR AUTOMATIC CRITICAL EVENT NOTIFICATION

(75) Inventors: Myron M. Shabot, Culver City, CA (US); Mark Lobue, Palm Dale, CA (US)

(73) Assignee: Cedars-Sinaimedical Center, Los Angeles, CA (US)

Reexamination Request:
No. 90/009,587, Sep. 25, 2009

Reexamination Certificate for:
Patent No.: 5,942,986
Issued: Aug. 24, 1999
Appl. No.: 08/512,887
Filed: Aug. 9, 1995

(51) Int. Cl.
*G06F 19/00* (2006.01)
*G06F 17/00* (2006.01)
*G06F 159/00* (2006.01)
*H04Q 7/18* (2006.01)

(52) U.S. Cl. ............... 340/7.29; 340/539.1; 340/539.18; 340/7.59; 370/313; 379/38; 600/513; 600/515; 600/523; 706/924

(58) Field of Classification Search .................. None
See application file for complete search history.

(56) References Cited

U.S. PATENT DOCUMENTS

| 4,550,726 A | 11/1985 | McEwen |
| 4,751,726 A | 6/1988 | Hepp et al. |
| 5,003,984 A | 4/1991 | Muraki et al. |
| 5,036,852 A | 8/1991 | Leishman |
| 5,128,979 A | 7/1992 | Reich et al. |
| 5,228,449 A | 7/1993 | Christ et al. |

(Continued)

OTHER PUBLICATIONS

Shabot et al., "Decision Support Alerts for Clinical Laboratory and Blood Gas Data", International Journal of Clinical Monitoring & Computing, vol. 7, pp. 27–31; Kluwer Academic Publishers, Netherlands, 1990.*

Gottschalk et al., "MIB Software—Semantic Model ASN.1 Messaging for a Pulse Oximeter", Proceedings of the Fourteenth Annual Symposium on Computer Application in Medical Care, pp. 220–225; IEEE Computer Society Press, Los Alamitos, USA, Nov. 7, 1990.*

Fumai, Nicola, "A Database for an Intensive Care Unit Patient Data Management System", Thesis, McGill University; National Library of Canada, Canadian Theses Service Ottawa, Canada, 1992.*

*Primary Examiner*—B. James Peikari

(57) ABSTRACT

A critical event notification system continuously monitors patient statistics and lab data to detect critical events, and automatically pages a responsible physician or physicians, each having an alphanumeric pager. In particular, a computer is used to continually access real-time data and multiple hospital databases which are periodically updated. These databases include patient chart databases, databases corresponding to patient history and databases maintained by various labs. The computer, preferably a clinical information system, is automatically provided with certain data, or periodically extracts it from other, relational databases. The computer automatically reviews this data, makes the critical event determination, and formulates an alphanumeric message that is informative as to the patient's condition and the reasons why a critical event was detected. After automatically retrieving from a database a personal identification number ("PIN") for a remote pager of each physician responsible for the patient, the computer automatically establishes modem contact with a paging network, and causes the network to page each responsible physician and transmit to them the alphanumeric message. The alphanumeric message preferably indicates patient name, diagnosis, the event prompting the page, and the name and return telephone number of medical personnel at the hospital who are attending the particular patient.

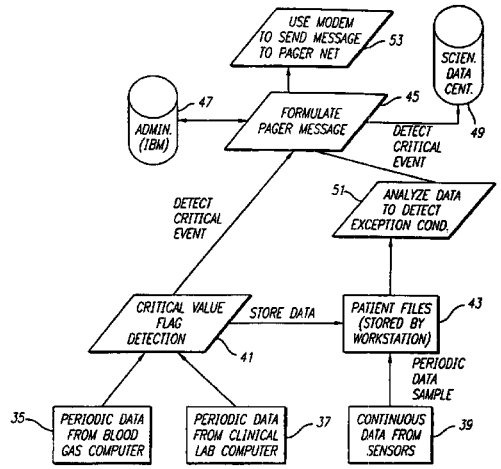

U.S. PATENT DOCUMENTS

| | | |
|---|---|---|
| 5,307,263 A | 4/1994 | Brown |
| 5,319,355 A | 6/1994 | Russek |
| 5,319,363 A | 6/1994 | Welch et al. |
| 5,331,549 A | 7/1994 | Crawford, Jr. |
| 5,348,008 A | 9/1994 | Bornn et al. |
| 5,357,427 A | 10/1994 | Langen et al. |
| 5,390,238 A | 2/1995 | Kirk et al. |
| 5,404,292 A | 4/1995 | Hendrickson |
| 5,416,695 A | 5/1995 | Stutman et al. |
| 5,430,440 A | 7/1995 | Shim |
| 5,447,164 A | 9/1995 | Shaya et al. |
| 5,522,387 A | 6/1996 | Simons |
| 5,534,851 A | 7/1996 | Russek |
| 5,544,661 A | 8/1996 | Davis et al. |
| 5,549,113 A | 8/1996 | Halleck et al. |
| 5,576,952 A | 11/1996 | Stutman et al. |
| 5,579,001 A | 11/1996 | Dempsey et al. |
| 5,579,775 A | 12/1996 | Dempsey et al. |
| 5,592,945 A | 1/1997 | Fiedler |
| 5,740,800 A | 4/1998 | Hendrickson et al. |
| 5,781,442 A | 7/1998 | Engleson et al. |
| 5,942,986 A | 8/1999 | Shabot et al. |

\* cited by examiner

EX PARTE
REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 23 is cancelled.

Claims 1-6, 8, 13 and 19-21 are determined to be patentable as amended.

Claims 7, 9-12, 14-18, 22, 24 and 25, dependent on an amended claim, are determined to be patentable.

New claims 26-38 are added and determined to be patentable.

1. An automatic critical event notification system, comprising:
   a remote pager having a display screen and an identification number;
   a paging system that selectively transmits a message to the remote pager using the identification number, to cause the remote pager to display the message;
   data representing variable values of a [parameter] *plurality of different measurement parameters*; and
   a computer system electronically coupled to the paging system that is configured to unsolicitedly by not receiving instruction from the remote pager,
      automatically receive the data *representing the variable values,* and determine [whether the values of the parameter have] *that a complex condition exists when each of said values concurrently has* a predetermined relation with respect to a predefined quantity *for its respective measurement parameter*,
      automatically formulate a particular message that indicates the existence of the [relation] *complex condition*, in response to the determination [that values of the parameter satisfy the relations] and
   automatically send the particular message to the paging system in electronic format, together with the identification number for the remote [device] *pager*;
   wherein the paging system automatically pages the particular remote pager identified by the identification number and sends to [it] *said pager* the particular message indicating the existence of the [relation] *complex condition*.

2. A system according to claim 1, wherein:
   the data represents values of a *plurality of different* patient [statistic] *statistics;*
   each *of* the predefined [quantity] *quantities* is a value of one *of* the [statistic] *statistics* that represents a change in the condition of the patient for which it is appropriate to notify a physician; and
   each *of* the predetermined [relation] *relations* represents values of the patient statistic which are one of greater than, less than and equal to *one of* the predefined [quantity] *quantities*.

3. A system according to claims 1 or 2, wherein:
   [the system further comprises data for each one of a plurality of different parameters;
   the predetermined relation is satisfied only when data for each one of the plurality of different parameters meets a predefined condition; and
   the computer system is configured to, with respect to each one of the plurality of different parameters, compare data representing the corresponding one of the parameters with a corresponding predefined quantity, to determine whether the predetermined relation is satisfied] *data received for a particular patient indicate that one of the predetermined relations for the particular patient exists when at least one of the variable values of the plurality of different measurement parameters for the particular patient has persisted beyond a defined length of time*.

4. A system according to claims 1 or 2, wherein:
   the system further comprises a plurality of data inputs, each corresponding to a different medical patient, the data inputs each representing measurement of the same patient statistic, *said patient statistic indicating a value of a measurement parameter*;
   the computer system includes a table that indicates a responsible user for each patient and a unique identification number for a remote pager corresponding to each user;
   the computer system is configured to determine whether the [relation exists for each of the plurality of data inputs] *predetermined relations exist*;
   identify, responsive to a determination that the [relation exists] *predetermined relations concurrently exist* for a particular patient, a particular identification number that corresponds to the pager of a user corresponding to the particular patient; and
   automatically, without receipt of instruction from a pager of a user, formulate and send the alphanumeric message to the user corresponding to the particular patient, via the paging network.

5. An automatic critical event notification system, comprising:
   detection means for unsolicitedly and electronically comparing *each of a plurality of* data inputs, *each* having *a* variable [values] *value*, with at least one predefined quantity, to determine the existence of a predetermined relation;
   message means for formulating an alphanumeric message that indicates [the] *a* predetermined state, in response to the existence of the predetermined relation; and
   remote transmission means for transmitting the alphanumeric message to [the] *a* remote message receiving device in response to the existence of the predetermined relation;
   wherein the predetermined relation is automatically [detected from] *determined by* the [data] *detection means* and the alphanumeric message is automatically, without receipt of instruction from a remote message receiving device, electronically formulated and transmitted to the remote message receiving device, *wherein the detection means includes multiple parameter means for receiving the data inputs and for ascertaining a complex condition, wherein a complex condition is ascertained to exist when each of the plurality of data*

*inputs concurrently has the predetermined relation to its corresponding pre-defined quantity.*

6. A system according to claim 5, [wherein:] *each of the data inputs representing a different parameter,* the [detection means includes] multiple parameter means [for receiving a plurality of data inputs, each representing a different parameter, and for] determining and distinguishing each one of a plurality of predetermined relations, each relation corresponding to a condition relative to one or more parameters represented by the data inputs;

the message means includes multiple message means for formulating a different alphanumeric message for each predetermined relation in response to detection of such relation by the detection means; and the remote transmission means receives each alphanumeric message formulated by the multiple message means and includes sending means for sending each alphanumeric message to the remote receiving device;

wherein each predetermined relation is automatically detected from the plurality of data inputs and a corresponding alphanumeric [messages] *message* is automatically and electronically formulated and transmitted to the remote message receiving device.

8. An automatic critical event notification system used to notify at least one of a plurality of users as to a critical event representative of the condition of at least one of a plurality of patients, comprising:

a remote pager carried by each user, each remote pager having an alphanumeric display and a unique personal identification number;

a pager network adapted to receive a message and a pager number sent via a communication device, the pager network responsive to selectively send the message to a particular remote pager identified by the pager number;

a database that receives electronic data representing each patient's condition;

a computer system having a communication device, wherein the computer system, is configured to unsolicitedly, by not receiving instruction from the remote pager carried by each user, and automatically monitor the database with respect to each one of the plurality of patients, to detect whether *for a given patient,* the data [for represents] *represent* a critical event and responsively indicate a detected critical event, *wherein the data represent and responsively indicate a detected critical event when the data concurrently indicate the presence of a plurality of different patient conditions;* formulate an alphanumeric message indicating the existence of the detected critical event, determine a user responsible for the care of the patient corresponding to the detected critical event and identifying the particular personal identification number which corresponds to that user, and control the communication devie of the computer system to establish an electronic link with the pager network and send the particular personal identification number to the pager network as the pager number, and send the alphanumeric message to the pager network;

wherein the pager network is automatically responsive to the computer system to send the alphanumeric message to the remote pager of the user responsible for the care of the particular patient, and the alphanumeric display of the pager displays the alphanumeric message to thereby indicate the existence of the [predetermined relation] *detected critical event,* thereby notifying the user of the [predetermined relation] *detected critical event* without requiring a real-time human decision to page the user.

13. A system according to claims 1 [,] *or* 5 [or 8], wherein:

the predetermined [relation] *relations* also [includes] *include* the relation of averaged data being one of less than, greater than, and equal to the predefined quantity; and the computer system includes a memory and software that causes it to store the data in the memory, periodically interrogate the memory to average the data samples to thereby produce the averaged data, and compare the averaged data with the predefined quantity to detect the existence of the predetermined relation.

19. A method of automatically nofitying an individual of the existence of a critical [value of a measurement parameter,] *event* using a computer system, a remote pager and a paging network, the computer system having a communications device that permits it to selectively communicate with the paging network, comprising:

using the computer system to automatically and unsolicitedly monitor data, *including data* representing [the] *a plurality of different* measurement [parameter] *parameters* by receiving that data [with] *at* the computer system and automatically [comparing] *determining whether or not each subset of* the data *representing one of the plurality of measurement parameters* has a predefined relation with a *corresponding* predefined quantity to detect the existence of [the] *a* critical [value] *event,* [thereby indicating] *wherein* the existence of [a] *the* critical event *is ascertained when a plurality of said predefined relations exist*;

in response to detection of the existence of the critical event and without receipt of instruction from the remote pager, causing the communications device to automatically establish a communications link between the paging network and the computer system; and using the computer to transmit a message to the paging network which causes the paging network to automatically notify the remote pager.

20. A method of automatically notifying an individual having a remote pager with alphanumeric display capabilities of the existence of a critical event, said method using a paging network that can receive instructions to page the remote pager and transmit to it an alphanumeric message, a source of data and a computer system that is electrically connected to the source of data, said method comprising:

using the computer system to automatically, unsolicitedly, by not receiving instructions from a remote pager, and electronically receive the data from the data source and automatically check the data to detect the existence of a critical value in the data, to thereby determine that the critical event has occurred, *wherein the critical event is ascertained to have occurred when the data concurrently meet a plurality of different patient conditions,* upon detection of the critical value, automatically formulating with the computer system an alphanumeric message indicating the existence of the critical event, causing the computer system to automatically establish a communications link with the paging network, causing the computer system to transmit the alphanumeric message to the paging network;

wherein the paging network upon receipt of the message automatically transmits the alphanumeric message to the remote pager, and said method automatically detects the critical event and causes the remote pager to display the alphanumeric message indicating the existence of the critical event without requiring a human decision to page the remote pager.

21. A method according to [claims] *claim* 19 [or 20], wherein *one of* the measurement [parameter] *parameters* represents a patient statistic, and wherein the computer system is coupled to an electronic sensor that electronically measures the patient statistic and produces the data, the method further comprising:
periodically sampling the electronic sensor with the computer system to produce a series of sequential data samples representing the patient statistic over time; and
comparing the series of sequential data samples with the predefined quantity to determine the existence of the critical value.

26. A system according to claim 1 or 5, wherein said plurality of different measurement parameters relate to patient conditions and one of said plurality of said measurement parameters based on which a complex condition is ascertained to exist includes the persistence of a patient condition beyond a defined length of time.

27. A system according to claim 26, wherein the plurality of said measurement parameters based on which a complex condition is ascertained to exist include heart and respiration rates, or systolic blood pressure and pulmonary artery wedge pressure, or ventilator oxygen component and PEEP.

28. A method according to claim 19, wherein said plurality of different measurement parameters relate to patient conditions and one of said plurality of said measurement parameters based on which a complex condition is ascertained to exist includes the persistence of a patient condition beyond a defined length of time.

29. A method according to claim 28, wherein the plurality of said measurement parameters based on which a complex condition is ascertained to exist include heart and respiration rates, or systolic blood pressure and pulmonary artery wedge pressure, or ventilator oxygen component and PEEP.

30. The system of claim 1 or 5, wherein the message describes the nature of the complex condition.

31. The system of claim 1 or 5, wherein the computer system is configured to formulate and send the message indicating the existence of the complex condition only when a complex condition is detected.

32. The system of claim 8, wherein the alphanumeric message describes nature of the detected critical event.

33. The system of claim 8, wherein the computer system is configured to formulate and send the alphanumeric message indicating the existence of the detected critical event only when a critical event is detected.

34. The system of claim 8, wherein the computer system is programmed to allow definition of said critical condition on a patient by patient basis, based on medical conditions of patients, and to use alerting algorithms to determine the existence of the critical event based on such definition.

35. The system of claim 34, wherein the definition of the critical condition for a patient is different from the definition of such condition for another patient.

36. An automatic critical event notification system used to notify at least one of a plurality of users as to a critical event representative of the condition of at least one of a plurality of patients, comprising:
a remote pager carried by each user, each remote pager having an alphanumeric display and a unique pager identification number;
a pager network adapted to receive a message and a pager identification number, the pager network adapted to selectively send the message to a particular remote pager as identified by the pager identification number;
a database that receives electronic data representing each patient's condition;
a computer system wherein the computer system, is configured to unsolicitedly, by not receiving instruction from the remote pager carried by each user, and automatically, carry out the following steps without requiring a real-time human decision to page the user,
monitor the database with respect to each one of the plurality of patients, to detect whether or not the data for any of said patients represents a critical event;
formulate an alphanumeric message indicating the existence of the detected critical event,
determine a user responsible for the care of the patient corresponding to the detected critical event and
identify the particular personal identification number which corresponds to that user, and
control the computer system to establish an electronic link with the pager network and
send the particular personal identification number to the pager network as the pager number, and
send the alphanumeric message to the pager network;
wherein the pager network is automatically responsive to the computer system to send the alphanumeric message to the remote pager of the user responsible for the care of the particular patient, the alphanumeric display of the pager displays the alphanumeric message thereby, notifying the user of the detected critical event, and
wherein the computer system is programmed to allow definition, for each patient, of the critical event, and wherein the critical event is defined to have occurred when a predefined set of patient conditions is concurrently present.

37. The system of claim 36, wherein the definition of the critical event for a patient is different from the definition of such condition for another patient.

38. The system of claim 8, wherein said critical event is one where the data indicates persistence of a patient condition beyond a defined length of time.

* * * * *